United States Patent
Wang et al.

(10) Patent No.: US 12,067,715 B2
(45) Date of Patent: Aug. 20, 2024

(54) PATIENT ANATOMY AND TASK SPECIFIC AUTOMATIC EXPOSURE CONTROL IN COMPUTED TOMOGRAPHY

(71) Applicants: GE Precision Healthcare LLC, Milwaukee, WI (US); The Board of Trustees of the Leland Stanford Junior University, Stanford, CA (US)

(72) Inventors: Adam S. Wang, Palo Alto, CA (US); Debashish Pal, Sunnyvale, CA (US); Abdullah-Al-Zubaer Imran, Sunnyvale, CA (US); Sen Wang, Menlo Park, CA (US); Evan Zucker, Palo Alto, CA (US); Bhavik Natvar Patel, Paradise Valley, AZ (US)

(73) Assignees: GE PRECISION HEALTHCARE LLC, Waukesha, WI (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 421 days.

(21) Appl. No.: 17/471,420

(22) Filed: Sep. 10, 2021

(65) Prior Publication Data
US 2023/0080631 A1  Mar. 16, 2023

(51) Int. Cl.
*G06T 7/00* (2017.01)
*A61B 6/00* (2006.01)
(Continued)

(52) U.S. Cl.
CPC ............ *G06T 7/0012* (2013.01); *A61B 6/032* (2013.01); *A61B 6/542* (2013.01); *A61B 6/545* (2013.01);
(Continued)

(58) Field of Classification Search
CPC ......... G06T 7/0012; G06T 2207/10081; G06T 2207/10144; G06T 2207/20081;
(Continued)

(56) References Cited

U.S. PATENT DOCUMENTS

| 8,045,771 B2 | 10/2011 | Tao |
| 10,368,825 B2 | 8/2019 | Crotty |

(Continued)

FOREIGN PATENT DOCUMENTS

| CN | 102451014 A | 5/2012 |
| WO | 2015105944 A1 | 7/2015 |
| WO | 2021155342 A1 | 8/2021 |

OTHER PUBLICATIONS

EP application 22192553.0 filed Aug. 29, 2022—extended Search Report issued Feb. 6, 2023, 7 pages.
(Continued)

*Primary Examiner* — Shefali D Goradia
(74) *Attorney, Agent, or Firm* — Amin, Turocy & Watson, LLP

(57) ABSTRACT

Techniques are described for tailoring automatic exposure control (AEC) settings to specific patient anatomies and clinical tasks. According to an embodiment, computer-implemented method comprises receiving one or more scout images captured of an anatomical region of a patient in association with performance of a computed tomography (CT) scan. The method further comprises employing a first machine learning model to estimate, based on the one or more scout images, expected organ doses representative of expected radiation doses exposed to organs in the anatomical region under different AEC patterns for the CT scan. The method can further comprises employing a second machine learning model to estimate, based on the one or more scout images, expected measures of image quality in target and background regions of scan images captured under the
(Continued)

different AEC patterns, and determining an optimal AEC pattern based on the expected organ doses and the expected measures of image quality.

20 Claims, 27 Drawing Sheets

(51) Int. Cl.
*A61B 6/03* (2006.01)
*G06N 3/08* (2023.01)
*G06N 20/00* (2019.01)
*G06V 10/25* (2022.01)

(52) U.S. Cl.
CPC ............... *G06N 3/08* (2013.01); *G06N 20/00* (2019.01); *G06V 10/25* (2022.01); *G06T 2207/10081* (2013.01); *G06T 2207/10144* (2013.01); *G06T 2207/20081* (2013.01); *G06T 2207/30168* (2013.01)

(58) Field of Classification Search
CPC .......... G06T 2207/30168; G06N 20/00; G06N 3/08; G06V 10/25; A61B 6/032; A61B 6/542; A61B 6/545
See application file for complete search history.

(56) References Cited

U.S. PATENT DOCUMENTS

| | | | | |
|---|---|---|---|---|
| 11,615,879 | B2* | 3/2023 | Do | G06V 20/20 382/128 |
| 2018/0018757 | A1* | 1/2018 | Suzuki | G06N 3/045 |
| 2020/0094074 | A1 | 3/2020 | Chen | |
| 2022/0130520 | A1* | 4/2022 | Xia | G06T 7/0014 |
| 2023/0036222 | A1 | 2/2023 | Fu et al. | |

OTHER PUBLICATIONS

Badal et al., "Accelerating Monte Carlo Simulations of Photon Transport in a Voxelized Geometry Using a Massively Parallel Graphics Processing Unit", Medical Physics, vol. 36, No. 11, Nov. 2009, pp. 4878-4880.
Brook et al., "CT Scout View as an Essential Part of CT Reading", Australasian Radiology, vol. 51, No. 3, Jul. 2007, pp. 211-217.
Chen et al., "Rethinking Atrous Convolution for Semantic Image Segmentation", arXiv:1706.05587v3 [cs.CV], 2017, 14 pages.
Çiçek et al., "3D U-Net: Learning Dense Volumetric Segmentation From Sparse Annotation", International Conference on Medical Image Computing and Computer-Assisted Intervention, Oct. 17-21, 2016, pp. 424-432.
Damilakis, J., "CT Dosimetry: What Has Been Achieved and What Remains to be Done", Investigative Radiology, vol. 56, No. 1, Jan. 2021, doi. 10.1097/RLI.0000000000000727, 7 pages.
Dutta et al., "Assessment of Optimal Deep Learning Configuration for Vertebrae Segmentation from CT Images", Medical Imaging 2019: Imaging Informatics for Healthcare, Research, and Applications, vol. 10954, 2019, 1 page.
Fan et al., "Data-Driven Dose Calculation Algorithm Based on Deep U-Net", Physics in Medicine & Biology, vol. 65, No. 24, 2020, 12 pages.
Furhang et al., "A Monte Carlo Approach to Patient-Specific Dosimetry", Medical physics, vol. 23, No. 9, Sep. 1996, pp. 1523-1529.
Götz et al., "A Deep Learning Approach to Radiation Dose Estimation", Physics in Medicine & Biology, vol. 65, No. 3, 2020, 12 pages.
Gu et al., "CE-Net: Context Encoder Network for 2D Medical Image Segmentation", IEEE Transactions on Medical Imaging, vol. 38, No. 10, Oct. 2019, pp. 2281-2292.
Guerreiro et al., "Deep Learning Prediction of Proton and Photon Dose Distributions for Paediatric Abdominal Tumours", Radiotherapy and Oncology, vol. 156, 2021, pp. 36-42.
Kachelrieß et al., "Is It Possible to Kill the Radiation Risk Issue in Computed Tomography?" Physica Medica: European Journal of Medical Physics, vol. 71, Mar. 1, 2020, pp. 176-177.
Kontaxis et al., "DeepDose: Towards a Fast Dose Calculation Engine for Radiation Therapy Using Deep Learning", Physics in Medicine & Biology, vol. 65, No. 7, 2020, 11 pages.
Lee et al., "Deep-dose: A Voxel Dose Estimation Method Using Deep Convolutional Neural Network for Personalized Internal Dosimetry", Scientific Reports, vol. 9, No. 1, 2019, 9 pages.
Lell et al., "Recent and Upcoming Technological Developments in Computed Tomography: High Speed, Low Dose, Deep Learning, Multienergy", Investigative Radiology, vol. 55, No. 1, 2020, pp. 8-19.
Lin et al., "Focal Loss for Dense Object Detection", Proceedings of the IEEE International Conference on Computer Vision (ICCV), Oct. 2017, pp. 2999-3007.
Maier et al., "Real-Time Patient-Specific CT Dose Estimation using a Deep Convolutional Neural Network", 2018 IEEE Nuclear Science Symposium and Medical Imaging Conference Proceedings (NSS/MIC), Nov. 2018, pp. 1-3.
Offe et al., "Evaluation of Deep Learning Segmentation for Rapid, Patient-Specific CT Organ Dose Estimation Using an LBTE Solver", Medical Imaging 2020: Physics of Medical Imaging, vol. 11312, 1 page.
Valentin, J., "The 2007 Recommendations of the International Commission on Radiological Protection", ICRP Publication 103, Mar. 2007, 35 pages.
Ronneberger et al., "U-Net: Convolutional Networks for Biomedical Image Segmentation", Medical Image Computing and Computer-Assisted Intervention (MICCAI), Springer International Publishing, 2015, pp. 234-241.
Sharma et al., "A Real-Time Monte Carlo Tool for Individualized Dose Estimations in Clinical CT", Physics in Medicine & Biology, vol. 64, No. 21, Nov. 4, 2019, 22 pages.
Wang et al., "Acuros CTS: A Fast, Linear Boltzmann Transport Equation Solver for Computed Tomography Scatter—Part II: System Modeling, Scatter Correction, and Optimization", Medical Physics, May 2018, vol. 45, No. 5, pp. 1914-1925.
Zhu et al., "A Preliminary Study of a Photon Dose Calculation Algorithm Using a Convolutional Neural Network", Physics in Medicine & Biology, vol. 65, No. 20, Oct. 15, 2020, 10 pages.
Notice of Allowance received for U.S. Appl. No. 17/471,532, dated Jan. 24, 2024, 40 pages.

* cited by examiner

PATIENT ANATOMY AND TASK SPECIFIC AUTOMATIC EXPOSURE CONTROL IN COMPUTED TOMOGRAPHY

TECHNICAL FIELD

This application relates to medical image computed tomography (CT) scan optimization and more particularly to techniques for tailoring automatic exposure control settings to specific patient anatomies and clinical tasks.

BACKGROUND

Computed tomography (CT) has been one of the most successful imaging modalities and has facilitated countless image-based medical procedures since its invention decades ago. CT accounts for a large amount of ionizing radiation exposure, especially with the rapid growth in CT examinations. Therefore, it is desirable to reduce the CT radiation dose. However, the reduction in dose also incurs additional noise and with the degraded image quality, diagnostic performance can be compromised.

In this regard, radiation dose and image quality have traditionally been competing objectives in CT imaging. To balance the two, modern CT systems use automatic exposure control (AEC), particularly tube current modulation (TCM) based on scout images. However, the goal of conventional AEC algorithms is to provide a uniform noise level across the entire imaged volume. While this is generally successful in avoiding excessive radiation dose and maintaining image quality, it is largely based solely on the general shape and size of the patient. In addition, conventional AEC algorithms use a metric for dose which reflects the tube output rather than actual dose to the patient. Conventional AEC techniques remain unaware of patient-specific anatomy that impacts organ dose, do not account for image quality based on the task, and are prone to issues such as patient centering.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are provided that facilitate tailoring AEC settings to specific patient anatomies and clinical tasks using machine learning techniques.

According to an embodiment, a system is provided that comprises a memory that stores computer executable components, and a processor that executes the computer executable components stored in the memory. The computer executable components comprise a reception component that receives one or more scout images captured of an anatomical region of a patient in association with performance of a CT scan of the anatomical region of the patient, wherein the anatomical region comprises one or more organs. The computer executable components further comprise a dose estimation component that employs one or more first machine learning models to estimate, based on the one or more scout images, expected organ doses representative of expected radiation doses exposed to the one or more organs under different AEC patterns for the CT scan.

The one or more first machine learning models comprise a deep learning model trained using a supervised machine learning process and ground truth data comprising a plurality of CT volumes generated from CT scans of the anatomical region under the different AEC patterns and organ segmentation dose maps generated from the CT volumes. In some implementations, the computer executable components further comprise a training component that trains the deep learning model using the supervised machine learning process.

In some embodiments, the computer executable components further comprise a quality estimation component that employs one or more second machine learning models to estimate, based on the one or more scout images, expected measures of image quality in a target region and a background region of scan images captured under the different AEC patterns. The quality estimation component determines the target region and the background region based on a defined clinical task associated with the performance of the CT scan, wherein the target region and the background region vary for different clinical tasks. The one or more second machine learning models comprise a second learning model trained using a supervised machine learning process and ground truth data image quality data generated using a plurality of CT volumes generated from CT scans of the anatomical region under the different AEC patterns, wherein the ground truth image quality data provides measures of image quality in the target region and the background region as represented in the CT volumes under the different AEC patterns. In some implementations, the computer executable components further comprise a training component that trains the second deep learning model using the supervised machine learning process. The computer executable components can further comprise a simulation component that generates simulated noise projections using the CT volumes and generates the ground truth image quality data based on the simulated noise projection.

The computer executable components can further comprise an optimization component that determines an optimal AEC pattern of the different AEC patterns for the performance of the CT scan based on the expected organ doses and the expected measures of image quality in a target region, wherein the optimal AEC pattern maximizes image quality in the target region and minimizes radiation doses to the organs. In this regard, the different acquisition parameter values for one or more acquisition parameters selected from the group consisting of: tube current modulation (TCM), tube voltage, collimation, filtration, bowtie, pitch, and start angle.

According to an embodiment, another system is provided that comprises a memory that stores computer executable components, and a processor that executes the computer executable components stored in the memory. The computer executable components comprise a training component that trains a first deep learning network to determine expected organ doses representative of expected radiation doses exposed to one or more organs of an anatomical region under different AEC patterns of a CT scan based on one or more scout images captured of the anatomical region for different patients. The training component further trains a second deep learning network to determine expected measures of image quality in target regions and background regions of scan images captured under the different AEC patterns based on the scout images. The computer executable components further comprise an optimization component that employs the first deep learning network and the second deep learning network to determine optimal AEC patterns of the different AEC patterns for the CT scan that maximize image quality in the target regions and minimize radiation doses to the one or more organs.

The target regions and the background regions vary for different clinical tasks. In some implementations, the training component can further train a third deep learning network to determine the optimal AEC pattern for each scout image and clinical task combination. The computer executable components can further comprise an inferencing component that employs the third deep learning network to determine the optimal automatic exposure pattern for a new CT scan of the anatomical region of a patient based on one or more new scout images captured of the anatomical region of the patient and a selected task of the different clinical tasks.

In accordance with another embodiment, another system is provided that comprises a memory that stores computer executable components, and a processor that executes the computer executable components stored in the memory. The computer executable components comprise a reception component that receives task information identifying a clinical task associated with performance of a CT scan of an anatomical region of a patient, and one or more scout images captured of the anatomical region. The computer executable components further comprise an optimization component that determines an optimal AEC pattern for the performance of the CT scan based on the task information, the one or more scout images and using one or more machine learning techniques, wherein the optimal automatic control pattern maximizes image quality in a target region of scan images generated from the CT scan and minimizes radiation doses to one or more organs included in the anatomical region.

The one or more machine learning techniques comprise employing a first deep learning network and a second deep learning network to determine the optimal AEC pattern from amongst different candidate AEC patterns for the CT scan that maximize the image quality in the target regions and minimize radiation doses to the one or more organs. The first deep learning network comprises one or more first machine learning models that estimate, based on the one or more scout images, expected organ doses representative of expected radiation doses exposed to the one or more organs under the different AEC patterns. The second deep learning network comprises one or more second machine learning models that estimate, based on the one or more scout images, expected measures of image quality in the target region and the background region of scan images captured under the different AEC patterns.

In various implementations, in addition to determining the optimal AEC pattern, the optimization component further determines an expected image quality in the target region under the optimal AEC pattern and expected radiation doses to the one or more organs under the optimal AEC pattern. In some implementations, the computer executable components further comprise an interface component that facilitates receiving user input adjusting one or more parameters of the optimal exposure control pattern, resulting in a modified AEC pattern, and wherein based on reception of the user input, the optimization component determines an updated expected image quality in the target region and updated expected radiation doses to the one or more organs under the modified AEC pattern. The interface component can also facilitate receiving user input identifying at least one of, a desired image quality for the target region and a desired radiation dose to the one or more organs, and wherein based on reception of the user input, the optimization component determines a modified AEC pattern that achieves the desired image quality and the desired radiation dose. The computer executable components further comprise a control component operatively coupled to an imaging device that performs the CT scan and that controls performance of the CT scan by the imaging device based on the optimal automatic exposure pattern.

In some embodiments, elements described in the disclosed systems and methods can be embodied in different forms such as a computer-implemented method, a computer program product, or another form.

DETAILED DESCRIPTION

Figure 1:
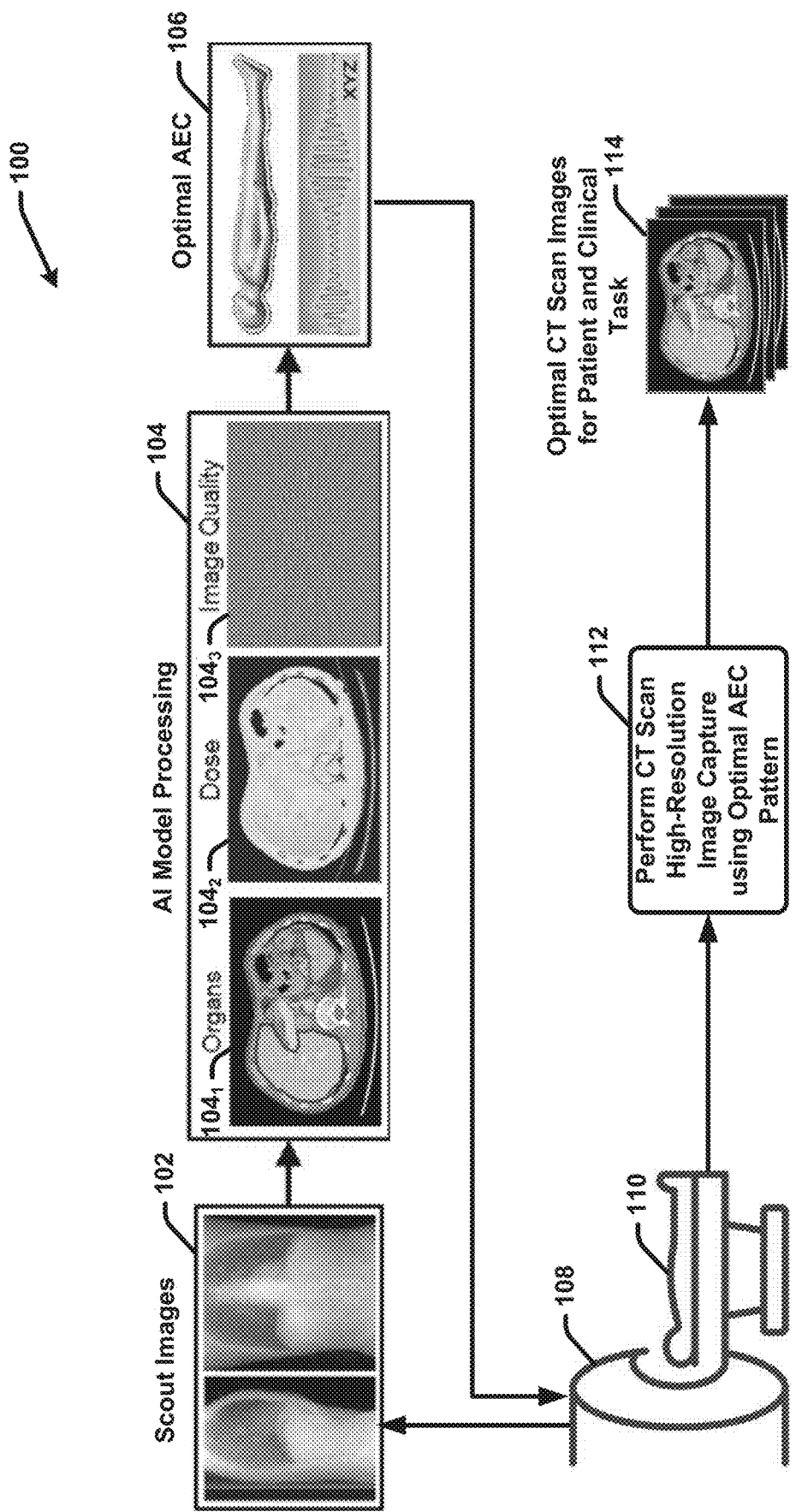
FIG. 1 illustrates a diagram of an example end-to-end process for tailoring the ACE setting of a CT scan based on the patient and clinical task in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that facilitate tailoring AEC settings to specific patient anatomies and clinical tasks. Conventional AEC techniques remain unaware of patient-specific anatomy that impacts organ dose, do not account for image quality based on the task, and are prone to issues such as patient centering. The proposed approach brings in an understanding of how different AEC settings affect organ dose and organ noise to optimize the tube current profile and other AEC parameters. This is enabled using deep learning technology. Access to organ level metrics make this approach more task and patient specific and in addition provides additional knobs for tube current optimization such as dose, advanced image quality features.

The disclosed AEC optimization techniques aim to maximize the relevant image quality for a fixed patient dose, or conversely, minimize dose while achieving the desired level of image quality. In going from generic to highly customized imaging protocols, the optimal AEC pattern for a particular CT scan focuses image quality (and radiation) where it is most needed while avoiding radiation-sensitive organs. The customization will be fully automated to integrate seamlessly with the workflow. Such personalized imaging accounts for patient and technical variability, which in return reduces variability in image quality to produce consistent, high-quality images.

Even with full volumetric information about the patient, this is not a trivial task, particularly if this is to be fast and automated. Current methods enable patient-specific organ dose calculation through computationally intense dose maps like Monte Carlo simulation and with the help of manual organ segmentation. They further require manual input on localizing where image quality should be focused and where it is less important. However, clinical workflow demands AEC be determined from scout images, and in a fast and automated manner. Using new AI methods and deep learning techniques, the disclosed AEC optimization strategy exploits the information in scout images to quickly and accurately predict patient-specific organ dose and image quality, thereby selecting the optimal AEC for the clinical task.

To facilitate this end, the disclosed techniques train a first deep learning model to directly infer organ doses from scout images and a prescribed AEC pattern. The training data uses matching CT volumes to compute the Monte Carlo dose map from the scan and segments the organs (e.g., using one or more organ segmentation models) to provide organ dose and total effective dose. The disclosed techniques further train a second deep learning model to infer image quality from the scout images and an AEC pattern. The image quality reflects expected image quality in different anatomical regions, such that the optimal AEC pattern can be tailored to optimize radiation and resulting image quality in a target region for the scan while minimizing radiation to the background region. The training data uses the same matching CT volumes to compute noise in projections and the resulting reconstructed images. In various embodiments, organ segmentation can also be used to map image quality metrics to the different organs, wherein the target regions and the background regions are based on the different organs.

The disclosed techniques further employ the first deep learning model and the second deep learning model to determine an optimal AEC pattern for a particular patient and clinical task that delivers the requested image quality at the minimum dose. The disclosed techniques further build an end-to-end optimization model that maps a given scout image and task to the optimal AEC in real-time. This optimization model can be integrated into the imaging workflow to automatically determine the optimal AEC for a CT scan in real-time based on the acquired scout images.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a diagram of an example end-to-end process 100 for tailoring the ACE setting of a CT scan based on the patient and clinical task in accordance with one or more embodiments of the disclosed subject matter. Process 100 is illustrated in accordance with performance of a CT scan of a patient 110 via an imaging system including a CT scanner 108. The type of the CT scanner can vary. For example, The CT scanner 108 can include a single energy scanner, a spectral CT scanner, and other types of CT scanners available in the industry.

In accordance with traditional CT imaging procedures, the patient is placed on the scanner table and the anatomy of interest is positioned around the center of the CT gantry. On or more scout images (e.g., scour images 102) are then acquired, and the operator marks the scan range (e.g., start and end locations) over which the scan is to be acquired. The correct scan protocol is then selected by the operator based on the clinical indication for the examination (e.g., contrast vs. non-contrast), and then the specific scan parameters are selected to produce scan images of the quality required for that diagnostic task. Finally, the scan images are captured and reconstructed using a range of parameters that determine the characteristics of the images, such as image sharpness and field of view (FOV).

With this context in mind, process 100 begins with the acquisition of scout images 102 of the patient 110 in association with positioning of the patient 110 relative to the CT scanner 108 gantry. These scout images 102 can include one or more low-resolution images captured of the patient's region of interest (ROI) to be scanned prior to capture of the subsequent high-resolution (e.g., isotropic) three-dimensional (3D) image data of the ROI and the generation of the corresponding high-resolution reconstructed CT scan images. These scout images 102 are generally used to position/align the scanner relative to a desired scan prescription plane for which the subsequent 3D image data is captured. The scout images 102 are also used to define the 3D imaging coverage volume or scan range for which the subsequent high-resolution scans are captured. In this regard, the scout images 102 can have a lower resolution/image quality relative to the subsequently acquired high-resolution scan images yet depict the same or wider region of interest. The terms "scout image," "localizer image," "calibration image," "pilot image," "reference image," and the like are used herein interchangeably unless context warrants particular distinction amongst the terms. Each of these terms refers to a medical image captured of an anatomical region of a patient having a lower resolution relative to the CT scan images captured of the anatomical region of the patient. In the embodiment shown, the scout images 102 include two different images captured from different anatomical orientations (e.g., lateral and frontal) relative to patient and the 3D imaging space. However, the number and orientation of the scout images 102 can vary. For example, in some embodiments, a single scout image can be used, while in other embodiments, two or more scout images can be used.

At 104, the scout images are processed using one or more AI models to determine an optimal AEC pattern 106 for the patient 110 and a specific clinical task for which the CT scan is being performed. The optimal AEC 106 defines parameters settings for the CT scan that control the radiation dose delivered to the patient and the resulting image quality of the scan images 114. In CT scans, there is always a trade-off between dose and image quality as images are acquired with the two competing objectives of maximizing image quality and minimizing radiation dose. The AI model processing at 104 tailors these AEC parameter settings to the patient 110 to account for the specific anatomy of the patient, which can vary based on patient size, shape, and the ROI being captured. The AI model processing at 104 also tailors these AEC setting to account for the specific region or regions of the resulting high resolution scan images that are important for clinical evaluation (e.g., detecting liver lesions on a non-contrast scan), which can vary from patient to patient and the ROI being scanned. In particular, the optimal AEC pattern is tailored to the patient anatomy to account for the estimated radiation doses exposed to the organs of the patient 110 included in the ROI under different AEC settings, as well as how these different AEC settings impact image quality in the specific region or regions of importance for clinical evaluation in the scan images. In this regard, the AI model processing at 104 involves determining the optimal AEC settings that result in focusing radiation exposure in regions where it is most needed for image quality and the clinical task, while avoiding or minimizing the amount of radiation delivered to radiation-sensitive organs.

In the embodiment shown, the AI model processing at 104 involves organ segmentation 1041, dose estimation 1042, and image quality 1043 estimation. At a high level, the organ segmentation 1041 involves using machine learning to automatically identify and segment the organs included in the scan ROI based on the scout images 102. The dose estimation 1042 involves using machine learning to predict how different AEC settings effect radiation doses to the organs. The image quality 1043 estimation involves using machine learning to predict how these different AEC settings and radiation doses also affect image quality in different regions of the scan images. The optimal AEC setting for the patient is then determined based on the organ dose and image quality estimations that minimizes radiation dose to the organs while also providing a desired level of image quality to the specific target region of importance for the clinical task. The optimal AEC setting evaluation and analysis can involve using one or more optimization functions as well as machine learning techniques. These machine learning and AI model processing techniques generally involve training one or more deep learning models to perform the segmentation 1041, the dose estimation 1042, and the image quality 1043 estimation prior to their usage in the clinical workflow depicted in process 100. Additional details regarding these machine learning and AI model processing techniques are described in greater detail below with reference to FIGS. 2-26.

The specific parameters of the optimal AEC pattern that are determined using the AI model processing at 104 can vary. There are many aspects to AEC, including the selection of the tube voltage or the tube current modulation (TCM), collimation, filtration, bowtie, pitch and start angle. TCM refers to the modulation pattern of the tube current over the course of a CT scan. Conventional AEC algorithms use TCM to increase the tube current (i.e., the number of x-ray photons) for thicker body regions and decrease the tube current for thinner body regions. As patients are not homogeneous cylinders, the end result is typically that the tube current oscillates up and down within a single rotation of the gantry, and increases, on average, through thick body regions (e.g., the shoulders and hips), and decreases, on average, through thinner body regions (e.g., the chest). In this regard, the TCM can be adjusted to dynamically control the number of photons at every projection through the patient.

The TCM significantly impacts radiation dose and corresponding image quality and can vary rapidly across multiple CT acquisition rotations as well as within a single rotation of the gantry. Thus, in various embodiments, the optimal AEC pattern 106 defines the optimal TCM settings for the CT scan that minimizes organ doses and maximizes image quality in the target region. However, the disclosed techniques are not limited to optimizing the TCM alone. In this regard, the optimal AEC 106 can reflect different acquisition parameter values for various additional CT acquisition parameters, including but not limited to: tube voltage (or tube potential), collimation, filtration, bowtie, pitch (or pitch factor), Z-axis coverage, source to detector distance, source to rotation axis distance, start angle, angle between projections, vertical translation between projections, polar and azimuthal apertures, and voxel spacings (isotropic). The start angle is of particular importance to helical scans. For example, because helical scans have highly non-uniform dose distributions, the start angle of helical CT scan be selected so that the beam avoids direct exposure of radiosensitive organs. The optimal AEC 106 can also account for different fluence field modulation strategies that extend beyond the current hardware capabilities, such as a laterally shifting bowtie, or even a dynamic bowtie. In this regard, the term "AEC pattern" is used herein to refer to the specific values of one or more CT scanner acquisition parameters that can be adjusted per scan and/or over the course of the CT scan (e.g., TCM). The terms "AEC pattern," "AEC settings," "AEC parameters," and the like are used herein interchangeably through the description unless context warrants particular distinction amongst the terms.

Once the optimal AEC has been determined based on the scout images 102, the system (or operating technician) can configure the CT scanner to perform the CT scan using the parameter values/settings defined by the optimal AEC. This configuration is performed prior to the performance of the actual CT scan (e.g., the actual acquisition of the 3D imaging CT data) while the patient is positioned on the scanning table. In this regard, in accordance with process 100, the optimal AEC can be determined and applied based on the scout images 102 in real-time at the start of the imaging session. At 112, imaging device (e.g., the CT scanner 108) can perform the CT scan of the high-resolution image capture using the optimal AEC pattern. The resulting scan images 114 will include optimal CT scan images for the patient and the clinical task. For example, the image quality (e.g., noise, resolution, etc.) of the scan images will be higher in the target region as opposed to the background region, wherein the target region represents the region of clinical relevance for the purpose of the CT scan (e.g., the anatomical region being targeted for clinical evaluation).

Figure 2:
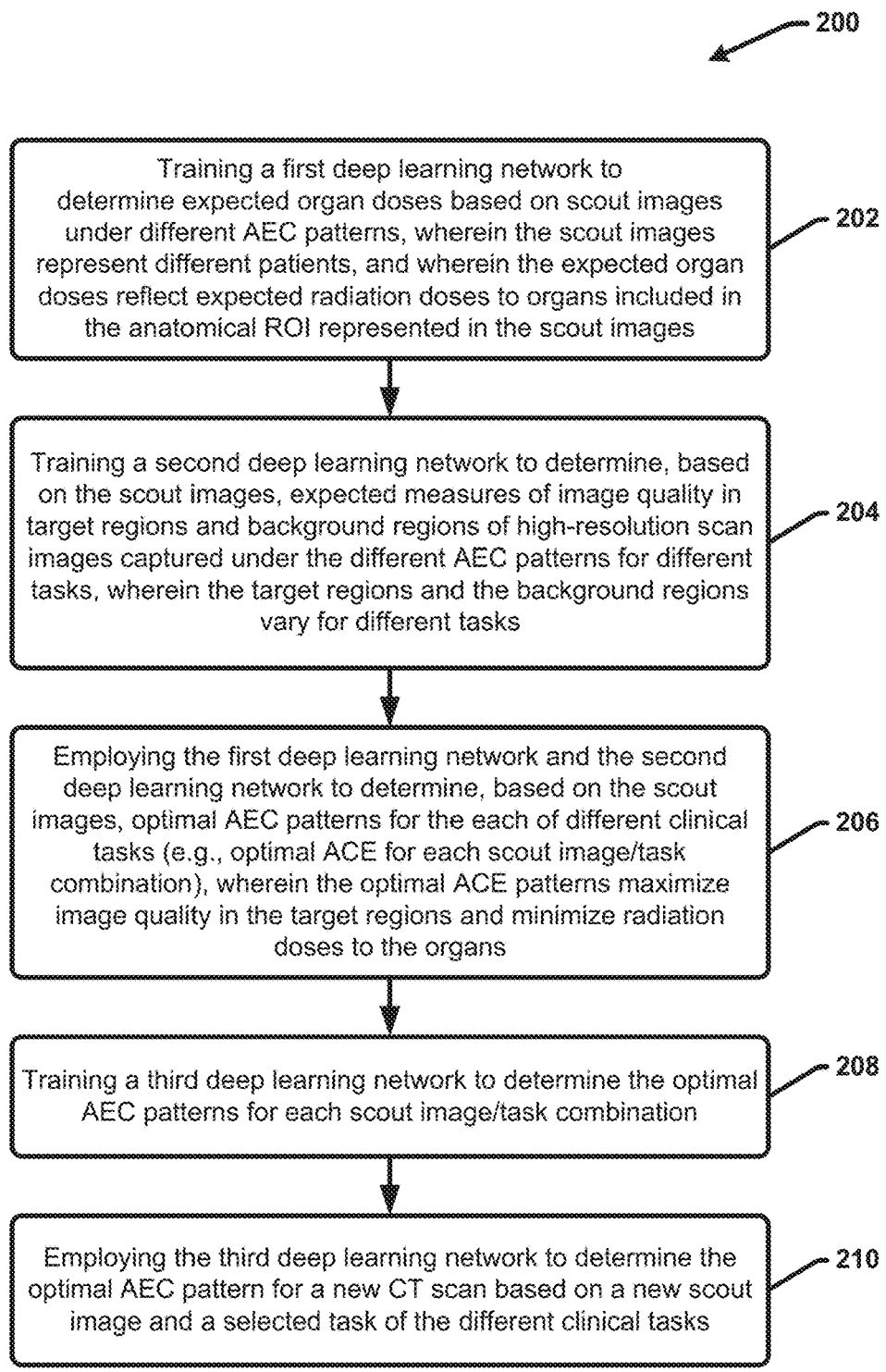
FIG. 2 presents a high-level flow diagram of an example machine learning process for generating patient and task customized AEC settings in accordance with one or more embodiments of the disclosed subject matter.

FIG. 2 presents a high-level flow diagram of an example machine learning process 200 for generating patient and task customized AEC settings in accordance with one or more embodiments of the disclosed subject matter. In various embodiments, one or more aspects of process 200 can be incorporated into the AI model processing 104 of process 100 to determine the optimal AEC 106.

In accordance with process 200, at 202, a first deep learning network is trained to determine expected organ doses based on scout images under different AEC patterns, wherein the scout images represent different patients, and wherein the expected organ doses reflect expected radiation doses to organs included in the anatomical ROI represented in the scout images. This first deep learning model is referred to herein as the dose estimation model. As described in greater detail below with reference to FIGS. 4-11, this training process uses matching CT volumes captured for each of the patients and their scout images to compute the Monte Carlo dose map from the scan and segments the organs (e.g., using one or more organ segmentation models) to provide organ dose and total effective dose. Once trained, the input to the dose estimation model can include one or more scout images, the scan range (or ROI) for the CT scan, and a selected AEC pattern. The output of the dose estimation model includes estimated radiation doses exposed to the organs in the ROI under the selected AEC pattern. In some embodiments, the dose estimation model can be tailored to a specific anatomical ROI (e.g., body part). With these embodiments, a plurality of different dose estimation models can be generated for different anatomical ROIs and/or CT scan types (e.g., abdomen, body, abdomen/pelvis, pelvis, CAP (chest, abdomen and pelvis), chest/abdomen, runoff, head, head/neck, C-spine, chest, extremity, TL-spine, L-spine, T-Spine, and facial bone). At runtime, the system can select an apply the appropriate dose estimation model based on the ROI being scanned.

At 204, a second deep learning model is trained to determine based on the scout images, expected measures of image quality in target regions and background regions of high-resolution scan images captured under the different AEC patterns for different tasks, wherein the target regions and the background regions vary for different tasks. This second deep learning model is referred to herein as a quality estimation model. In one or more embodiments, the training data for the quality estimation mode uses the same matching CT volumes to compute noise in projections and the resulting reconstructed images under the different AEC patterns. The reconstructed images are further segmented to identify the target regions and the backgrounds regions and the corresponding noise levels are mapped thereto. In various embodiments, the target regions and background regions can be based on organ segmentation. With these embodiments, organ segmentation can also be used to map the image quality metrics (e.g., noise levels) to the different organs. Once trained, the input to the quality estimation model can include one or more scout images, the scan range (or ROI) for the CT scan, the selected AEC pattern, and the selected task (e.g., which indicates the desired target region). The output of the quality estimation model includes estimated measures of image quality (e.g., measured as a function of noise levels and/or other quality evaluation metrics) in the target and background region under the selected AEC pattern. In implementations in which the target region corresponds to one or more organs, the measure of image quality can reflect image quality of the one or more organs in the scan images. In some embodiments, the quality estimation model can also be tailored to a specific anatomical ROI (e.g., body part). With these embodiments, a plurality of quality estimation models can be generated for different anatomical ROIs and/or CT scan types (e.g., abdomen, body, abdomen/pelvis, pelvis, CAP (chest, abdomen and pelvis), chest/abdomen, runoff, head, head/neck, C-spine, chest, extremity, TL-spine, L-spine, T-Spine, and facial bone). At runtime, the system can select an apply the appropriate quality estimation model based on the ROI being scanned.

Once the first (e.g., dose estimation) and second (e.g., quality estimation) deep learning networks have been trained to a desired level of performance, at 206 both networks can be employed to determine optimal AEC patterns for different patients and tasks based on their scout images. In this regard, based on the scout images, optimal AEC patterns for each of different clinical tasks (e.g., optimal ACE for each scout image/task combination) are determined, wherein the optimal ACE patterns maximize image quality in the target regions and minimize radiation doses to the organs. In various embodiment, the optimization analysis performed at 206 models the AEC using one or more optimization functions that balance the competing objectives of dose and image quality using defined optimization criteria for the dose and image quality metrics. For example, in some implementations, the optimization function can be configured to find the optimal ACE that maximizes the relevant image quality for a fixed patient dose. In other implementations, the optimization function can be configured to find the optimal ACE that minimizes dose while achieving a desired level of image quality.

In some embodiments, the optimization analysis described above can be performed at runtime (e.g., in the clinical workflow processes 100) to determine the optimal AEC for a new patient based on their scout images. With these embodiments, the system will iteratively apply the dose estimation model and the quality estimation model to the scout images under different AEC patterns to determine how different AEC pattern options impact expected organ doses and image quality in the target region. The system can further automatically select the optimal ACE based on model outputs using the optimization function and predefined or user selected optimization criteria for the dose and image quality metrics.

Additionally, or alternatively, at 208 the system can train a third deep learning network to determine the optimal AEC patterns for each of the training data scout image/task combinations evaluated at 206. In this regard, the optimal AEC for each scout image/task combination determined for the training data at 206 can be used as ground truth to training data to train the third deep learning network. Once trained, the input to the third deep learning network will include one or more scout images (e.g., with the scan range and/or ROI indicated relative to the scout images) and the task. The third deep learning network will further output the optimal AEC. In some implementations, the third deep learning network can also be configured to generate the expected organ doses and the expected image quality metrics for the target region and the background region under the optimal AEC. At 210, this third deep learning network can be employed in the clinical workflow to determine the optimal AEC pattern for a new CT scan based on one or more new scout images and a selected task of the different clinical tasks 210. With these embodiments, the AI model processing at 104 in accordance with process 100 may involve application of only the third deep learning network.

Figure 3:
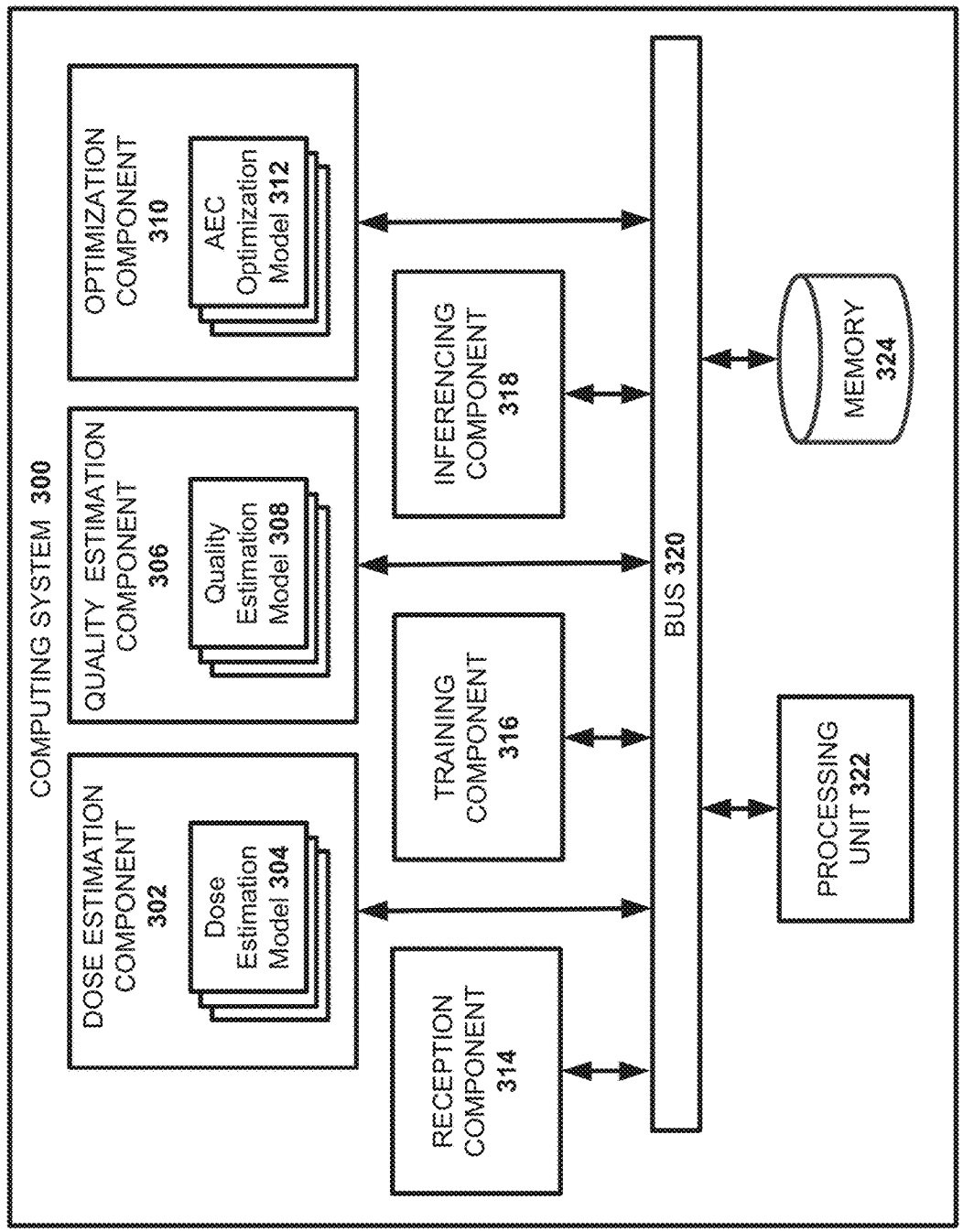
FIG. 3 presents an example computing system that facilitates tailoring AEC setting to specific patient anatomies and clinical tasks in accordance with one or more embodiments of the disclosed subject matter.

FIG. 3 presents an example computing system 300 that facilitates tailoring AEC setting to specific patient anatomies and clinical tasks in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

In this regard, computing system 300 provides an example computing system that includes machine-executable components configured to perform one or more of the operations described in process 100, process 200 and additional processes described herein. The computer executable components include a dose estimation component 302, one or more dose estimation models 304, a quality estimation component 306, one or more quality estimation models 308, an optimization component 310, one or more AEC optimization models 312, a reception component 314, a training component 316 and an inferencing component 318. These computer/machine executable components (and other described herein) can be stored in memory associated with the one or more machines. The memory can further be operatively coupled to at least one processor, such that the components can be executed by the at least one processor to perform the operations described. For example, in some embodiments, these computer/machine executable components can be stored in memory 324 of the computing system 300 which can be coupled to processing unit 322 for execution thereof. The computing system 300 further include a system bus 320 that communicatively and operatively couples the dose estimation component 302, the one or more dose estimation models 304, the quality estimation component 306, the one or more quality estimation models 308, the optimization component 310, the one or more AEC optimization models 312, the reception component 314, the training component 316, the inferencing component 318, the processing unit 316 and the memory. Examples of said and memory and processor as well as other suitable computer or computing-based elements, can be found with reference to FIG. 27, and can be used in connection with implementing one or more of the systems or components shown and described in connection with FIG. 3 or other figures disclosed herein.

The deployment architecture of computing system 300 can vary. In some embodiments, the computing system 300 can correspond a single computing device (e.g., real or virtual). In other embodiments, the computing system 300 can correspond to two or more separate communicatively coupled computing devices operating in a distributed computing environment. With these embodiments, one or more of the dose estimation component 302, the one or more dose estimation models 304, the quality estimation component 306, the one or more quality estimation models 308, the optimization component 310, the one or more AEC optimization models 312, the reception component 314, the training component 316, the inferencing component 318 can be deployed at separate computing devices. The separate computing devices can be communicatively coupled via one or more wired or wireless communication networks. In some implementations, the computing system 300 can include or be operatively coupled to the medical image scanning device (e.g., a CT machine such as the CT scanner 108 or the like) that performs the CT scanning procedure in association with capture of the scout images and the high-resolution CT scan images. Additionally, or alternatively, the computing system 300 can include a separate device/machine (e.g., real or virtual/cloud-based) that is communicatively coupled to the CT scanning device and/or an external image data storage system that provides the training data. Various alternative deployment architecture variations can also be used.

With reference to FIGS. 1-3, the dose estimation component 302 can perform the organ dose estimation operations described with reference to FIGS. 1 and 2. The quality estimation component 306 can perform the target and background region scan image quality estimation operations described with reference to FIGS. 1 and 2, and the optimization component 310 can perform the AEC optimization operations described with reference to FIGS. 1 and 2.

As described with reference to FIG. 2, the organ dose estimation, the image quality estimation, and (optionally) the AEC optimization can involve training separate machine learning models to perform the corresponding tasks. In the embodiment shown, these machine learning models respectively correspond to the one or more dose estimation models 304, the one or more quality estimation models 308 and the one or more AEC optimization models 312. To facilitate this end, the computing system 300 can include training component 310 that performs (or facilitates performing) the machine learning model training and development using one or more supervised or semi-supervised machine learning techniques. The computing system 300 can further include an inferencing component 312 that executes the trained models to generate their corresponding inference outputs. The computing system 300 further include a reception component 308 that receives training data (and/or the information used to generate the training data) for training the respective models and the input data for model execution following training. The features and functionalities of the dose estimation component 302 and the one or more dose estimation models 304 are described with reference to FIGS. 4-10. The features and functionalities of the quality estimation component 306 and the one or more quality estimation models 308 are described with reference to FIGS. 11-19, and the feature and functionalities of the optimization component 310 and the one or more AEC optimization models are described with reference to FIGS. 20-26. Repetitive description of like elements employed in respective embodiments is omitted for sake of brevity.

Organ Dose Estimation

Figure 4:
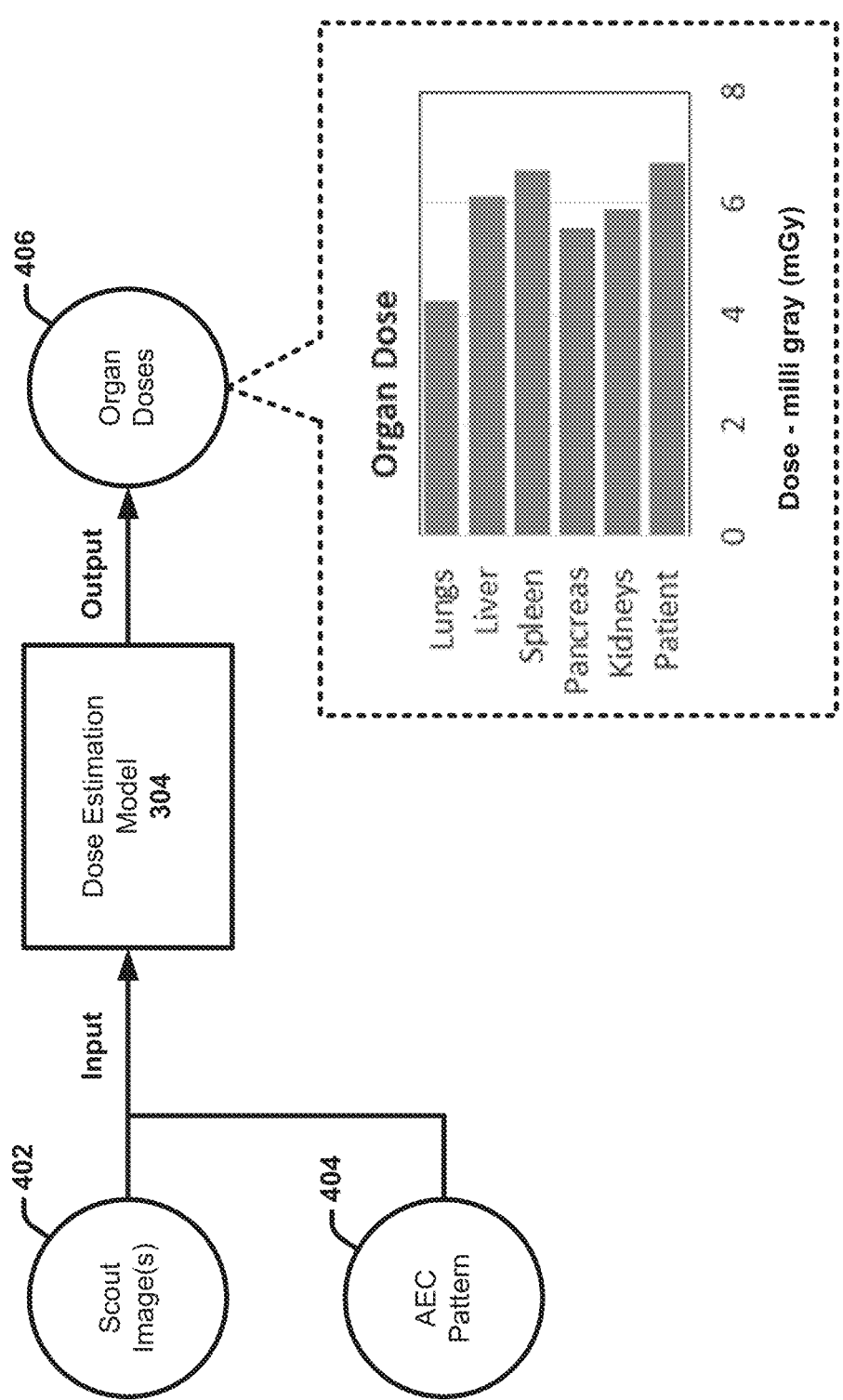
FIG. 4 presents an example dose estimation model in accordance with one or more embodiments of the disclosed subject matter.

FIG. 4 presents an example dose estimation model 304 in accordance with one or more embodiments of the disclosed subject matter. As illustrated in FIG. 4, the input to the dose estimation model 304 can include one or more scout images 402 and an AEC pattern. The one or more scout images 402 can include scout images captured of an anatomical region of a patient in association with performance of a CT scan of the anatomical region. In some implementations, the scout images 402 can provide different perspectives of the anatomical region (e.g., axial, sagittal, coronal, etc.). In other implementations, a single scout image can be used. The AEC pattern 404 can define selected parameter values for one or more AEC parameters in CT. In various embodiments, the AEC pattern 404 can define a specific TCM scheme for the CT scan. Additionally, or alternatively, the AEC pattern 404 can define specific parameter values for one or more other AEC parameters, including but not limited to: tube voltage (or tube potential), collimation, filtration, bowtie, pitch (or pitch factor), Z-axis coverage, source to detector distance, source to rotation axis distance, start angle, angle between projections, vertical translation between projections, polar and azimuthal apertures, and voxel spacings (isotropic).

The output of the dose estimation model 304 includes organ doses 406 that represent the estimated radiation doses absorbed by the organs of the patient in association with performance of the CT scan using the AEC pattern 404. The dose estimation model 304 can also provide an estimate of the total effective dose under the AEC pattern. Effective dose is calculated for the whole body. It is the addition of equivalent doses to all organs, each adjusted to account for the sensitivity of the organ to radiation. The effective dose is expressed in millisieverts (mSv). For example, the dose estimation model 304 can generate the effective dose (mSv) by combining the organ doses through a weighted sum of the organ doses using known International Commission on Radiological Protection (ICRP) tissue weighting factors.

The specific organs evaluated by the dose estimation mode are based on the particular organs included in the ROI of the patient scanned. In some implementations, the ROI can account for the entirety of the anatomical region represented in the scout images 402. In other implementations, the ROI can include a sub-region of the anatomical region depicted in the scout images. With these implementations, information defining the sub-region or scan range can also be provided as input with the scout images 402. In this regard, scout images are often used to position the patient relative to the CT gantry and define the scan range or portion of the body to be captured in the CT scan. The scouts are almost always longer than the actual scans. Since our goal is to predict the dose in the actual scans, a scan range signal can be included with the input data to inform the dose estimation model 304 about the focus region in the input scouts. This additional information makes the model informed about where to look at for dose estimation, given the input scout images. As described in greater detail infra, in estimating organ dose from the scout images 402, the dose estimation model 304 will implicitly learn organ segmentation as well to identify the relevant organs.

In this example, the organs evaluated include lungs, liver, spleen, pancreas and kidneys. These organs are generally scanned in association with performance of a CT scan of the abdomen. Thus, in this example, the ROI includes the patient's abdomen. However, the dose estimation model 304 can be trained to evaluate any anatomical ROI and the relevant organs associated therewith. The relevant organs for each anatomical ROI can be predefined. As mentioned above, in some embodiments, different dose estimation models 304 can be tailored to different anatomical ROIs. With these embodiments, during inferencing mode, the inferencing component 318 can select and apply the appropriate dose estimation model 304 for the particular ROI represented in the scout images. Additionally, or alternatively, the dose estimation model 304 can include a universal model configured evaluate any anatomical ROI. With these embodiments, the dose estimation model 304 can be trained to identify the relevant organs in any ROI and tailor organ dose estimation for those relevant organs.

The type or types of machine learning models used for the dose estimation model 304 can vary. In some embodiments, the dose estimation model 304 can include one or more deep learning models, such as convolutional neural network (CNN)s, RESNET type models, and other neural network models with different types of pooling techniques. For example, in one implementation, the dose estimation model 304 can employ a CNN architecture, followed by a fully connected layer and regression layer that outputs the organ specific doses and the total effective dose. Other suitable types of the machine learning models can include but are not limited to, generative adversarial neural network models (GANs), long short-term memory models (LSTMs), attention-based models, transformers, decision tree-based models, Bayesian network models, regression models and the like. These models may be trained using supervised, unsupervised and/or semi-supervised machine learning techniques.

Figure 5:
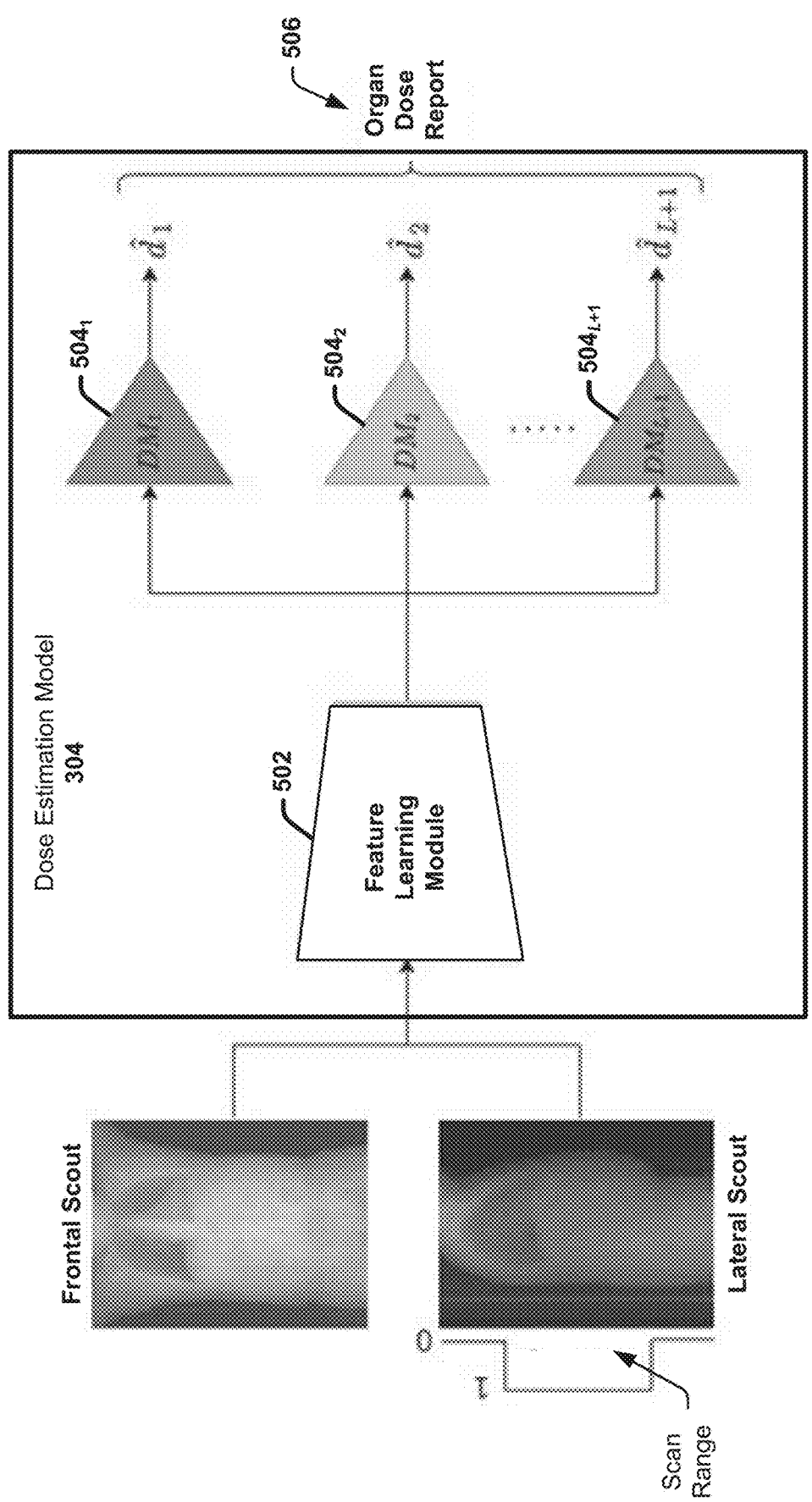
FIG. 5 presents an example dose estimation model architecture in accordance with one or more embodiments of the disclosed subject matter.

FIG. 5 presents an example dose estimation model architecture that can be used for the dose estimation model 304 in accordance with one or more embodiments of the disclosed subject matter. In accordance with this example, the dose estimation model 304 comprises a CNN-based model. In this example, the dose estimation model 304 is used to predict the CT dose distribution at organs-of-interest from input frontal and lateral scout views of the patient's body within the indicated scan range under different AEC settings. However, it should be appreciated that the anatomical ROI represented in the input scout images can vary and the number and type (e.g., orientation) of the input scout images can vary.

In the embodiment shown, the dose estimation model 304 comprises two modules: a feature learning module (FLM) 502 and multiple dose modules (DM) $504_1$-$504_{L+1}$, wherein L corresponds to the number of different organs evaluated. The FLM 502 is used to extract the shared features, later utilized through separate organ-specific DMs. In addition to organ dose prediction, the model also estimates the patient's overall body dose through a separate DM. Therefore, the dose outputs for the L different organs and patient (body) are generated via L+1 DMs (e.g., $DM_1$, DM2, . . . $DM_{L+1}$). All the predicted outputs are characterized by mean doses.

In one example implementation, the FLM module can include eight 3×3 convolutions with feature maps of 16, 16, 32, 32, 64, 128, 256, and 512 respectively with stride 2 in the second and fourth convolutions. Each of the convolutions can be followed by an instance normalization and a leaky ReLU activation with negative slope of 0.2. The feature maps can be downsized by half after every two convolutions via 2×2 maxpool operations. The CNN model can further include a global average pooling layer and the features can be drawn across the channels. The extracted features are then shared across the DMs. Each of DM modules may consist of two fully-connected (FC) layers (512 and 1.0 neurons respectively), a leaky ReLU activation with slope 0.2, and finally a sigmoid to output the mean dose prediction in the normalized scale.

In accordance with this example implementation, from the reference mean doses di and the model predicted doses $\hat{d}_l$ at an organ labeled as l (l∈L), the loss for the dose estimation model 304 is therefore calculated in accordance with Equation 1 below, where M denotes the minibatch size, and the patient body dose is denoted at (L+1)-th.

$$\mathcal{L}^{dose}_{(d,\hat{d})} = \frac{1}{M} \sum_i^M \sum_l^{L+1} \|d_l(i) - \hat{d}_l(i)\|_2.$$

Equation 1.

The reference organ dose values correspond to the ground truth information used to train the dose estimation model 304. In one or more embodiments, the disclosed techniques generate these reference values from actual CT scan data.

In particular, the training data used to train and generate (e.g., test and validate) the dose estimation model 304 can include a plurality of CT scans for different patients and their corresponding scout images captured before the CT scans. In some implementations, the scout images for the CT scans can include synthetically generated scout images. The CT scans (and their paired scout images) can respectively depict the same anatomical ROI in implementations in which the model is trained for a specific anatomical ROI (e.g., the abdomen). Additionally, or alternatively, the CT scans (and their paired scout images) can depict a variety of different anatomical ROIs. The CT scan data provides a 3D volume representation of the anatomical ROI.

In one or more embodiments, the GT (i.e. reference) organ dose values can be generated by processing the CT scan volumes are to compute dose maps for the CT scan volumes under different AEC patterns. In various embodiments, these dose maps can be generated using Monte Carlo (MC) simulations. The MC simulations can generate and track particles at the voxel level and the deposited energy is calculated for patient-specific estimation of absorbed dose. An accelerated MC simulation has been introduced through graphics processing unit (GPU) computation, referred to as MC-GPU, which can accurately model the physics of x-ray photon transport in voxelized geometries. The disclosed techniques configure this MC-GPU simulation method to account for different AEC patterns of CT scanners (e.g., existing and future CT scanners) and employ it to compute the dose maps for the CT volumes. In this regard, for a given protocol, the trajectory can be discretized into multiple source positions per rotation. The source output is then modeled for each position, accounting for the AEC parameter values, including the tube voltage, collimation, filtration, and bowtie. The dose map of each source position is further normalized per source photon, and then scaled according to the tube current and rotation time (mAs) represented by that source position. This enables flexible adjustment of the tube current modulation without having to re-run the MC simulation.

The organs are further segmented from these dose maps using one or more segmentation models to provide the organ specific GT dose values and the GT total effective dose. In this regard, in estimating organ dose from scout images, the organ dose model 304 will implicitly learn the organ segmentation. However, for training and testing purposes, the training component 316 will need ground truth organ segmentations for each CT volume, such as lung, heart, esophagus, stomach, intestines, liver, pancreas, spleen, kidneys, bladder, gonads, muscle, skin, and bone. In some embodiments, the organ segmentation models can include separate machine learning organ segmentation models (e.g., CNNs) that are specific to a particular organ. With these embodiments, the specific organ segmentation models that are applied can be based on the relevant organs included in the ROI. In other embodiments, the organ segmentation models can include ROI specific organ segmentation model adapted to segment all relevant organs included in a particular ROI. Still in other embodiments, the organ segmentation models can include a universal organ segmentation model that is adapted to segment relevant organs in CT data from any ROI. The organ segmentation and dose maps are combined to estimate the organ doses (mGy), and the organ doses are combined into effective dose (mSv) through a weighted sum of organ doses, using ICRP tissue weighting factors. The corresponding scout images for the CT volumes are then used to train the dose estimation model 304 to infers these organ doses and the effective dose for the different AEC patterns.

Figure 6:
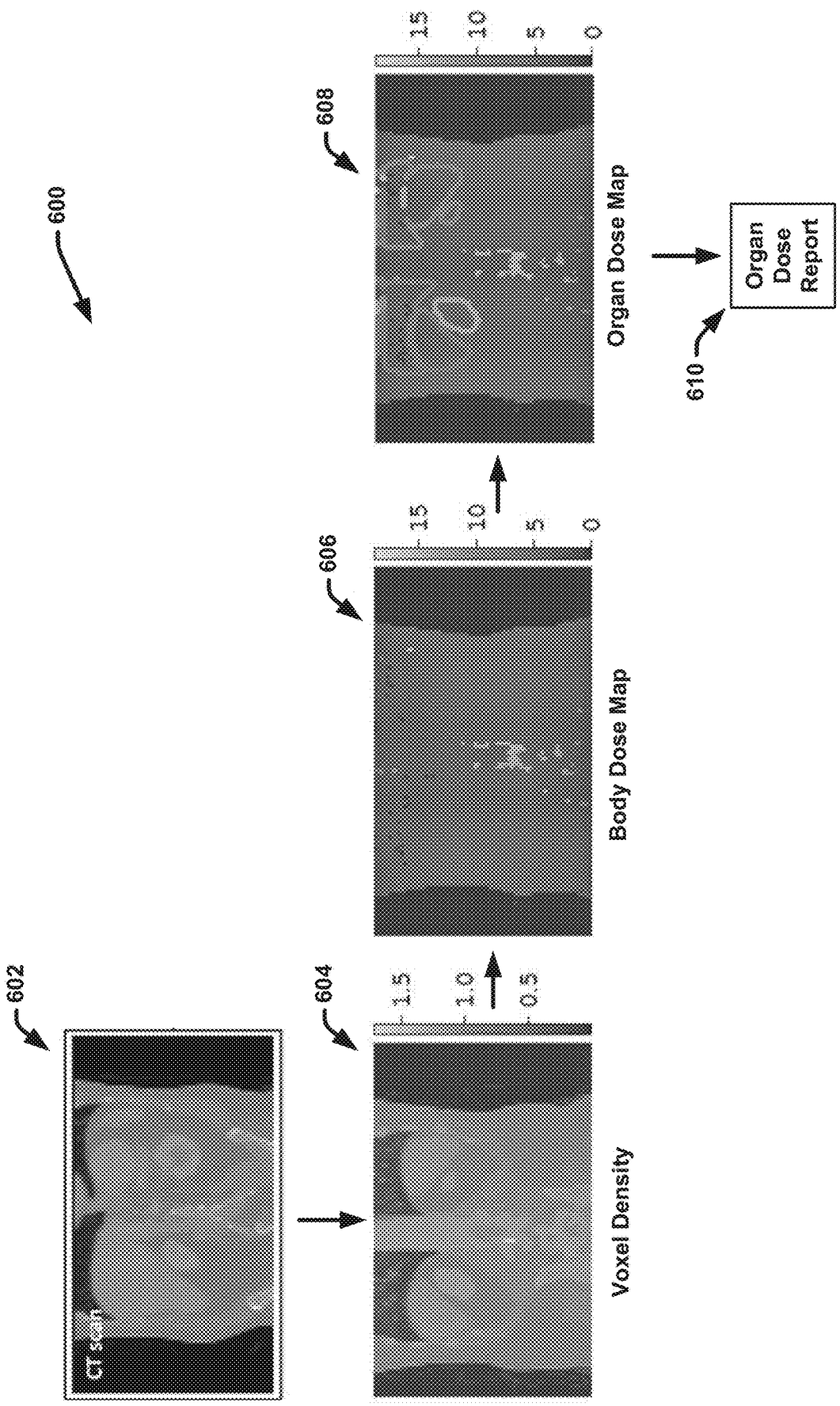
FIG. 6 illustrates an example pipeline for organ dose estimation from CT data in accordance with one or more embodiments of the disclosed subject matter.

FIG. 6 illustrates an example pipeline 600 for organ dose estimation from CT data in accordance with one or more embodiments of the disclosed subject matter. Pipeline 600 starts with a CT scan data 602 corresponding to a CT volume comprising a plurality of scan slices. Using an MC-GPU simulation method, the CT scan data 602 is used to compute a voxel density map 604 which is then used to compute the body dose map 606. The body dose map 606 is then segmented using an organ segmentation model to generate the corresponding organ dose map 608. The organ dose map 608 is further used to generate an organ dose report 610 that provides the individual organ doses and the effective dose for a specific AEC pattern.

In accordance with the embodiment shown in FIG. 6, the input CT scan data 602 was interpolated and resampled to 128×128 in for each scan slice. The voxel density map 604 was created as voxelized patient phantom by mapping the CT Hounsfield Units (HU) to water-equivalent density, with isotropic voxels of 4×4×4 $mm^3$ in accordance with Equation 2.

$$V = \frac{HU}{1000} + 1.$$

Equation 2

The MC-GPU process was further modified to include the bowtie filtration and anode heel effect. The anode heel effect leads to photon intensity variation for azimuthal angles that can be modeled as a probability function. The bowtie model is based on basis material decomposition so that the inputs for MC-GPU are the material attenuation coefficients and material thickness combinations at different fan angles. With these implementations, once the source spectrum is input, the filtered spectra and relative photon intensity distribution for all fan angles can be computed. Therefore, photon directions and energies can be sampled accordingly.

The modified MC-GPU enables the analytical calculation of the ground truth of the detected image given the bowtie model, the heel effect model, and the input spectrum. For individualized patient organ dose, the phantoms are generated from the patient CT voxel data. In this regard, the input phantom data for MC simulation can contain the spatial map of both material type and mass density. The density mapping is performed following a piece-wise linear curve which defines the densities of the mixture of water and bone.

In the embodiment shown in FIG. 6, a helical scan was be simulated from the most superior to most inferior slice, with a pitch factor of 0.99, an 80 mm Z-axis coverage, 24 views per rotation, a 120 kVp spectrum, and a constant tube current. It should be appreciated however that these AEC parameter values are merely exemplary and that the disclosed techniques can be applied to generate organ dose maps for different TCM schemes and other AEC parameters. In the embodiment shown in FIG. 6, the MC-GPU dose calculation was repeated with N=4 start angles (θ(i)) uniformly spaced apart and averaged to obtain the dose map in accordance with Equation 3.

$$D_{avg} = \frac{1}{n}\sum_{i}^{N} MCGPU(V, \psi)|_{\theta(i)},$$ Equation 3.

In Equation 3, $\Psi$ denotes the set of all the parameters used to configure the MC-GPU simulation. The dose is reported as eV/g/photon and can be scaled to mGy (1 eV/g/photon=3.79 mGy/100 mAs) using a scanner-specific calibration (e.g., CTDI measurement). The air was masked out the using a patient body mask with a threshold $t_{air}$=0.1 from the voxel geometry V to obtain the body dose map 606. Therefore, the final dose map D can be represented in accordance with Equation 4.

$$D=D_{avg} \cdot (V > t_{air})$$ Equation 4.

The CT scan 602 was then segmented using a segmentation model that leverages a 3D context encoder U-Net network. The context encoder utilized atrous convolution at different rates in the encoder network which enables capturing longer range information compared to the standard U-Net. The decoder of the segmentation model employed residual multi-kernel pooling which performs max-pooling at multiple FOVs. The segmentation model was trained separately for the L different organs. The encoder and decoder networks utilized 5 convolution blocks followed by down-sampling and up-sampling respectively. The final convolution was followed by a softmax activation. The segmentation model was trained with a focal categorical cross-entropy loss in accordance with Equation 5, wherein i iterates over the number of channels and t iterates over the number of voxels in the image patches.

$$L^{seg}_{(y,\hat{y})} = -\sum_{t}\sum_{i}\alpha(1-\hat{y}_{t,i})^{\gamma}y_{t,i}\log(\hat{y}_{t,i})$$ Equation 5.

A weight map $w_t$ was calculated to emphasize the voxels near the boundary of the reference in accordance with Equation 6, where d is the Euclidean distance from the closest label and wherein a and b are the weighting factors. Weighting factors a=2.0 and b=0.5 were chosen for the experiments. The weight map was further added to the loss function Equation 5.

$$w_t = a \cdot \exp(-b \cdot d_t) + 1$$ Equation 6.

In order to calculate the organ-specific doses, the model predicted segmentation mask ($\hat{y}$) was interpolated and resampled to align the voxel coordinates to the CT voxel geometry prepared for the MC-GPU. The organ-specific dose map $O_l$, $l \in L$ (e.g., organ dose map 608) was generated from the body dose map D (e.g., body dose map 606) of Equation 4 and segmentation mask ($\hat{y}$) in accordance with Equation 7.

$$O_l = D \cdot \hat{y}_l; \ l \in L$$ Equation 7.

The organ-specific reference dose distributions were then determined and characterized by mean dose ($d_l$=mean($O_l$)) as well as mean body dose ($d_{L+1}$=mean($O_{L+1}$)).

Figure 7:
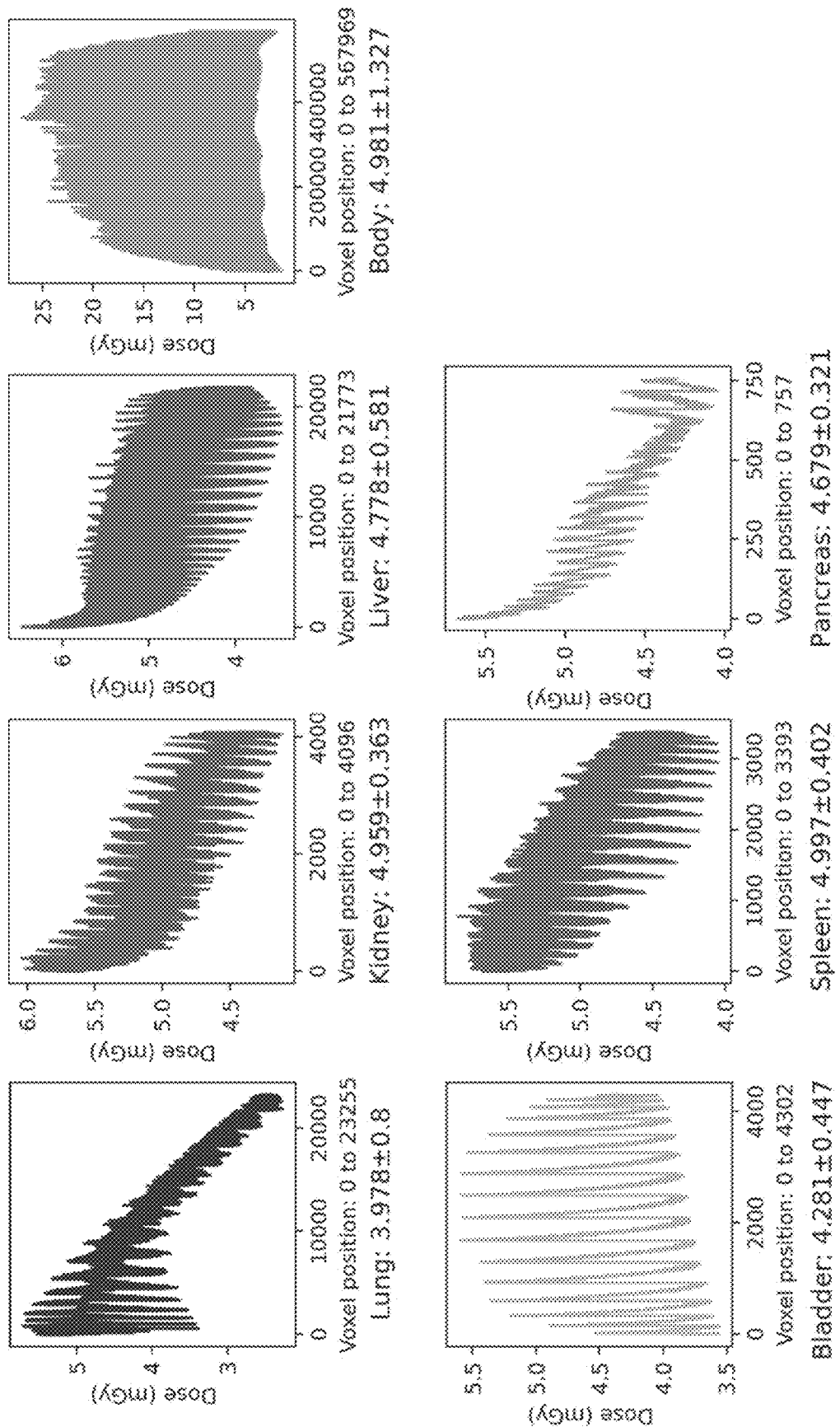
FIG. 7 illustrates organ specific dose report information generated from CT in accordance with one or more embodiments of the disclosed subject matter.

FIG. 7 illustrates organ specific dose report information generated from CT data using the techniques described above. In various embodiments, the organ dose report 610 can comprise the organ specific dose information illustrated in FIG. 7 for each of the respective segmented organs. In this example, the organ dose report data is demonstrated for the body and six different organs associated with an abdomen scan, including the lungs, kidney, liver, bladder, spleen and pancreas. The organ dose report data plots the absorbed dose in mGy for different voxel positions and provides the mean dose across all voxel positions.

Figure 8:
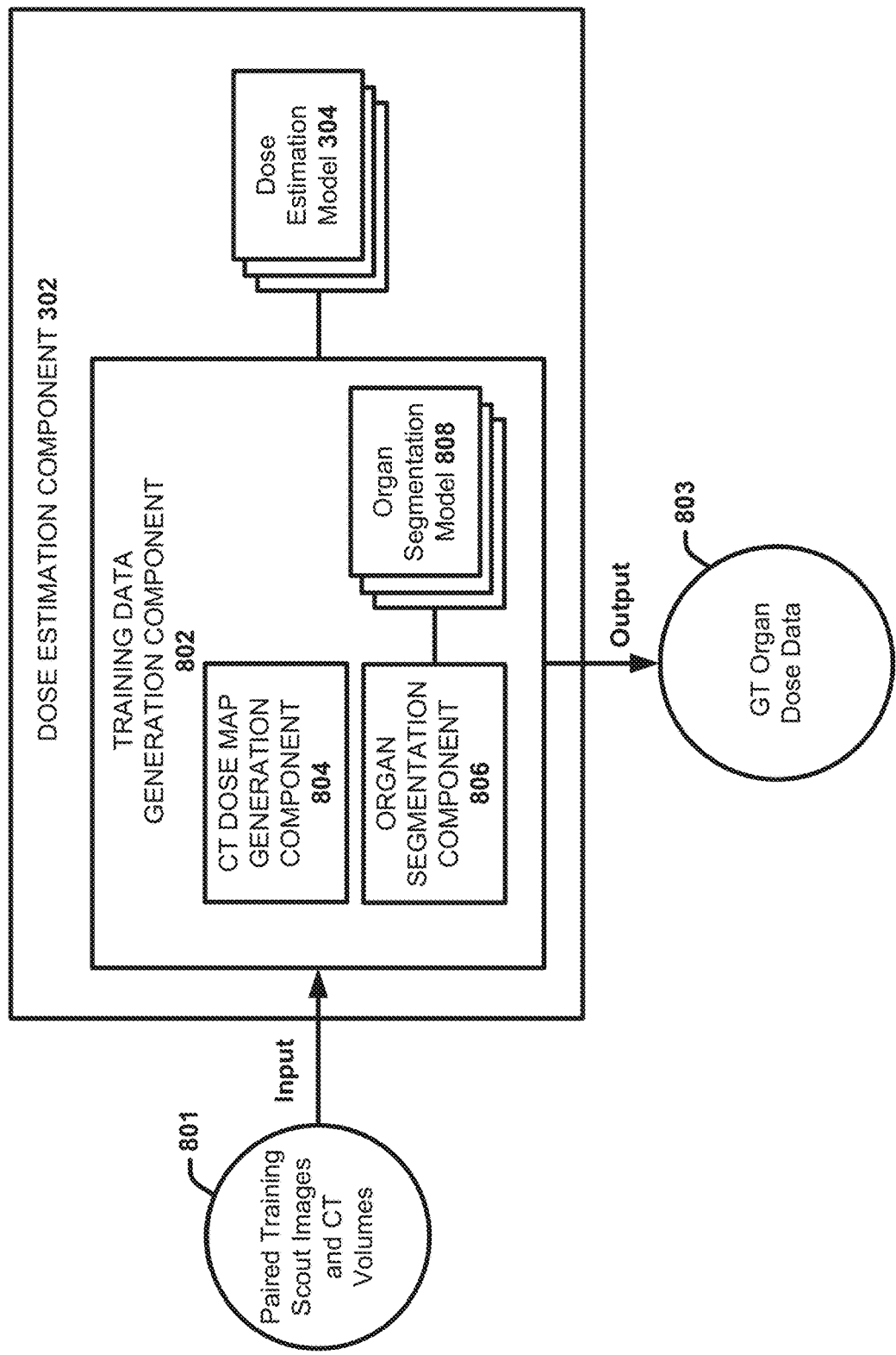
FIG. 8 presents an example dose estimation component in accordance with one or more embodiments of the disclosed subject matter.

FIG. 8 presents an example dose estimation component 302 in accordance with one or more embodiments of the disclosed subject matter. Repetitive description of like elements employed in respective embodiments is omitted for sake of brevity.

In some embodiments, the dose estimation component 302 can include training data generation component 802 to generate the ground truth organ and effective body dose value information in accordance with the MC simulation and organ segmentation methods described above. In this regard, the training data generation component 802 can receive paired training scout images and CT volumes 801 for different patients. The paired training scout images and CT volumes 801 can depict the same anatomical ROI in implementations in which the dose estimation model 304 is trained for a particular anatomical ROI. Using the CT volumes, the training data generation component 802 can generate the ground truth organ dose data 803 using the MC simulation and organ segmentation methods described above. This GT organ dose data 803 can include, for each of the training scout images (or groups of two or more implementations in which the input scout images include two or more, such as lateral and frontal for instance), organ doses and effective dose for one or more AEC patterns. To facilitate this end, the training data generation component 802 can include CT dose map generation component 804, organ segmentation component 806 and one or more organ segmentation models 808.

In this regard, using the MC-GPU simulation method described above and the CT volumes 801, the GT dose map generation component 804 can compute dose maps for each of the CT scan volumes. The computed dose maps for each CT volume can provide estimated 3D body dose maps (e.g., body dose map 606) for the anatomical ROI under different AEC patterns. For example, in one or more embodiments, for a given protocol, the CT dose map generation component 804 can discretize the photon trajectory into multiple source positions per rotation. The CT dose map generation component 804 can further model the source output for each position, accounting for the tube voltage, collimation, filtration, and bowtie. The CT dose map generation component 804 can further normalize the body dose map of each source position per source photon. The CT dose map generation component 804 can further scale the body dose map according to the tube current and rotation time (mAs) represented by that source position. The CT dose map generation component 804 can further adjust the TCM for different AEC patterns to generate the corresponding body dose map values without having to re-run the Monte Carlo simulation.

The organ segmentation component 806 can then apply one or more organ segmentation models 808 to the body dose maps to segment the relevant organs included in the ROI (e.g., which can be predefined) and generate the organ specific doses for the different AEC patterns along with the total effective body dose for each CT scan volume. As described above, in some embodiments, the organ segmentation models 808 can include a multi-organ segmentation model adapted to segment all the relevant organs for a specific anatomical ROI or any anatomical ROI. In other implementations, the organ segmentation models 808 can include separate models for each organ of interest.

Figure 9:
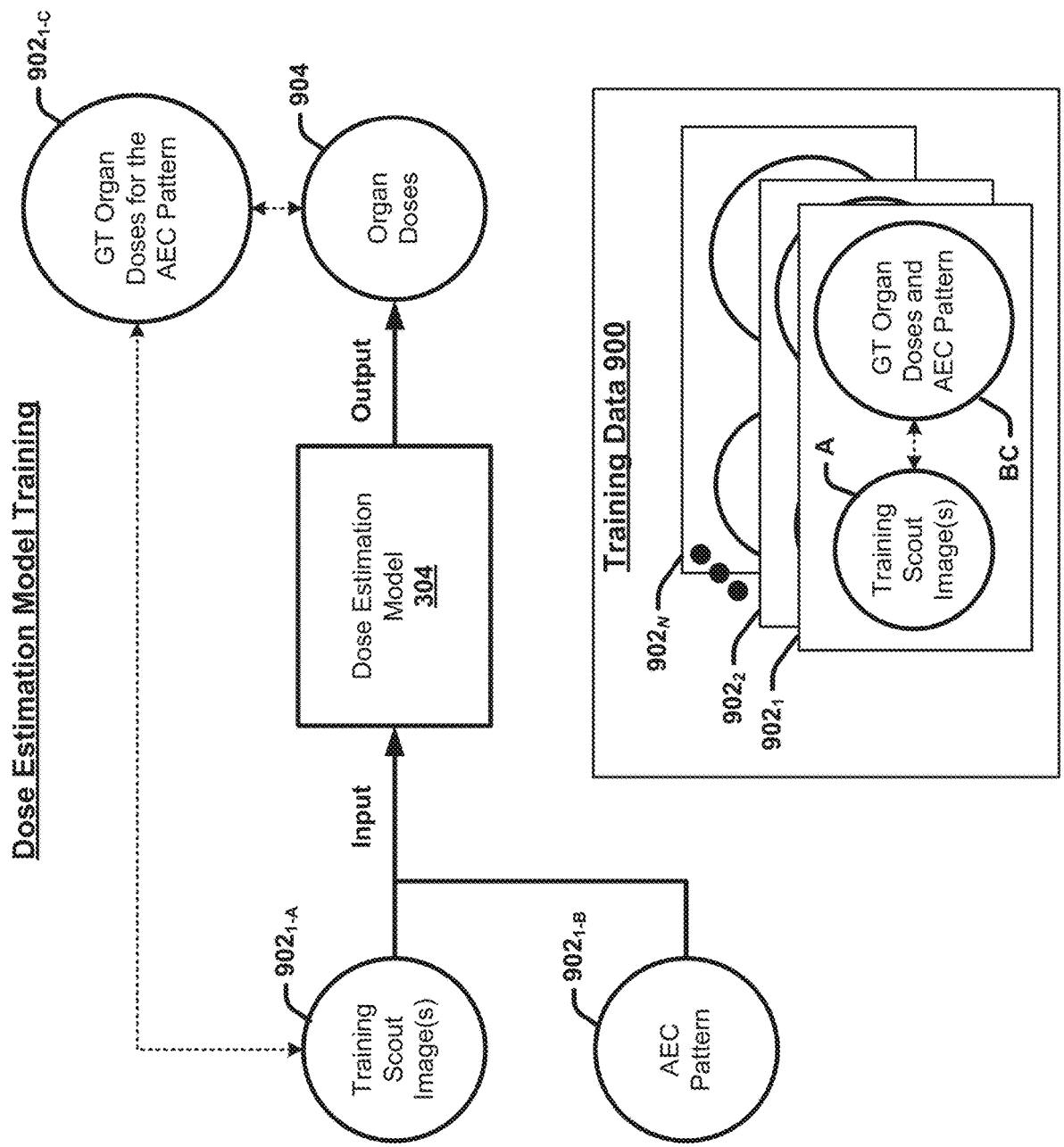
FIG. 9 illustrates dose estimation model training in accordance with one or more embodiments of the disclosed subject matter.

The GT organ dose data 803 and the paired scout images can then be used (e.g., by the training component 316) to train the one or more dose estimation models 304 to infers these organ doses and the total effective dose as illustrated in FIG. 9.

In this regard, FIG. 9 illustrates dose estimation model training in accordance with one or more embodiments of the disclosed subject matter. As illustrated in FIG. 9, the does estimation model training involves training the dose estimation model to predict the organ doses 904 (which can include the total effective dose) for a selected AEC pattern based on one or more scout images using the ground truth CT generated organ doses described above. With reference to FIGS. 3 and 9, in various embodiments, the training component 316 can perform the dose estimation model training illustrated in FIG. 9 using one or more supervised or semi-supervised machine learning training, testing and validation processes.

As illustrated in FIG. 9, the training data 900 can include a plurality of different training data sets, respectively identified as $902_{1-N}$. The number of training data sets N can vary. Each training data set includes three components respectively indicated with the letters A (component 1), B (component 2) and C (component 3). In particular, the first component A includes one or more scout images. In some implementations, the scout images can also include or otherwise be associated with information defining scan range. The second component B includes a known/defined AEC pattern, and the third component C includes the GT organ doses (and effective dose) determined for that AEC pattern. As discussed above, these GT organ doses are generated using CT volume data paired with the scout images A and the MC-simulated and organ dose map generated for the AEC pattern. In this regard, with respect to one example training data set $902_1$, the input to the dose estimation model 304 includes the AEC pattern $901_{1-B}$ and the one or more scout images $901_{1-A}$. The dose estimation model 304 is then trained to generate the estimated organ doses 904 using the GT organ doses for the AEC pattern $901_{1-C}$.

It should be appreciated that the collective training data sets $902_{1-N}$ represent scout images and paired CT volumes for different patients and different AEC patterns. Additionally, the collective training data sets $902_{1-N}$ can include groups of training data sets that include the same scout images (e.g., for the same patient), yet paired with GT organ doses (and effective dose) for different AEC patterns generated from the same paired CT volume data. The collective training data sets $902_{1-N}$ will also depict the same anatomical ROI when the dose estimation model 304 is trained for a specific anatomical ROI (e.g., the abdomen for example).

In one or more embodiments, for organs directly exposed by the beam, the target accuracy of the dose estimation model can be set to be within 5%, as this is a typical error even for MC dose calculations. Organs not directly exposed, but receiving dose from scatter, may have higher percent errors, though their absolute dose will be quite low. The total effective dose estimations can be set to be accurate within 1% since it averages errors across all organs. To improve the network performance and robustness, the training data 900 can also be augmented by randomly changing the 3D position of the CT volumes (and generating corresponding scout images), as well as using different AEC patterns.

Figure 10:
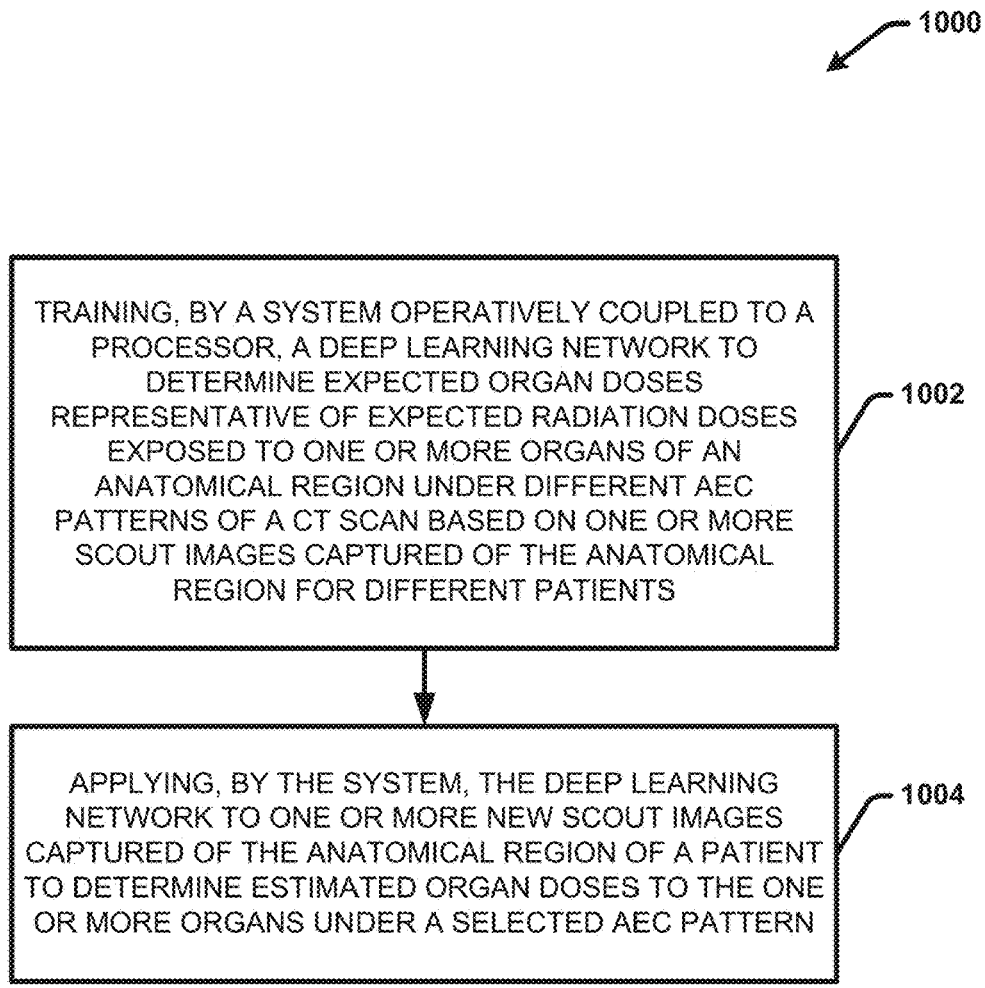
FIG. 10 presents a high-level flow diagram of an example process for estimating organ doses under a selected AEC pattern based on one or more scout images in accordance with one or more embodiments of the disclosed subject matter.

FIG. 10 presents a high-level flow diagram of an example process 1000 for estimating organ doses under a selected AEC pattern based on one or more scout images in accordance with one or more embodiments of the disclosed subject matter. Process 1000 provides an example process that can be performed by computing system 300 using reception component 314, training component 316, dose estimation component 302 and inferencing component 318. Repetitive description of like elements employed in respective embodiments is omitted for sake of brevity.

In accordance with process 1000, at 1002, a system operatively coupled to a processor (e.g., system 300 or the like) can train (e.g., by the dose estimation component 302 using training component 316 in accordance with FIG. 9), a deep learning network (e.g., a dose estimation model 304), to determine expected organ doses representative of expected radiation doses exposed to (or absorbed by) one or more organs of an anatomical region under different AEC patterns of a CT scan based on one or more scout images captured of the anatomical region for different patients. As described above, the training component 316 can train the dose estimation model using GT organ doses determined for the different patient and AEC pattern combinations. In some embodiments, prior to performing the training at 1002, process 1000 can also include generating the GT organ doses from matching CT volumes for the scout images using the MC simulated 3D dose maps under the different AEC patterns and subsequent organ segmentation of the 3D dose maps.

At 1004, once the deep learning network (i.e., the dose estimation model 304) has been trained, tested and validated, the system can apply (e.g., by the dose estimation component 302 using inferencing component 318) the deep learning network to one or more new scout images captured of the anatomical region of a patient to determine estimated organ doses to the one or more organs under a selected AEC pattern.

Image Quality Estimation

The organ dose estimation techniques described above provide the tools to quickly estimate organ doses for a given AEC pattern directly from scout images. In this section, we evaluate the impact of different AEC patterns and/or their resulting organ doses on image quality. For a given task, such as liver lesion detection on a contrast-enhanced scan, the disclosed techniques seek to maximize task-dependent image quality such as contrast-to-noise ratio (CNR) while maintaining sufficient image quality elsewhere. To facilitate this end, the disclosed techniques train a second deep learning network (e.g., one or more quality estimation models 308) to predict image quality in both the target and background regions from a patient's scout image. These techniques leverage the same training dataset of paired scout images and CT volumes described above for organ dose estimation, using the CT volumes to establish ground truth for image quality (IQ) in the target (IQ-target) and background (IQ-background) regions. Separately quantifying image quality in these regions enables the CT scanner to be selectively configured with an AEC pattern that provides high quality images in the target region while providing a baseline image quality in the background region.

Figure 11:
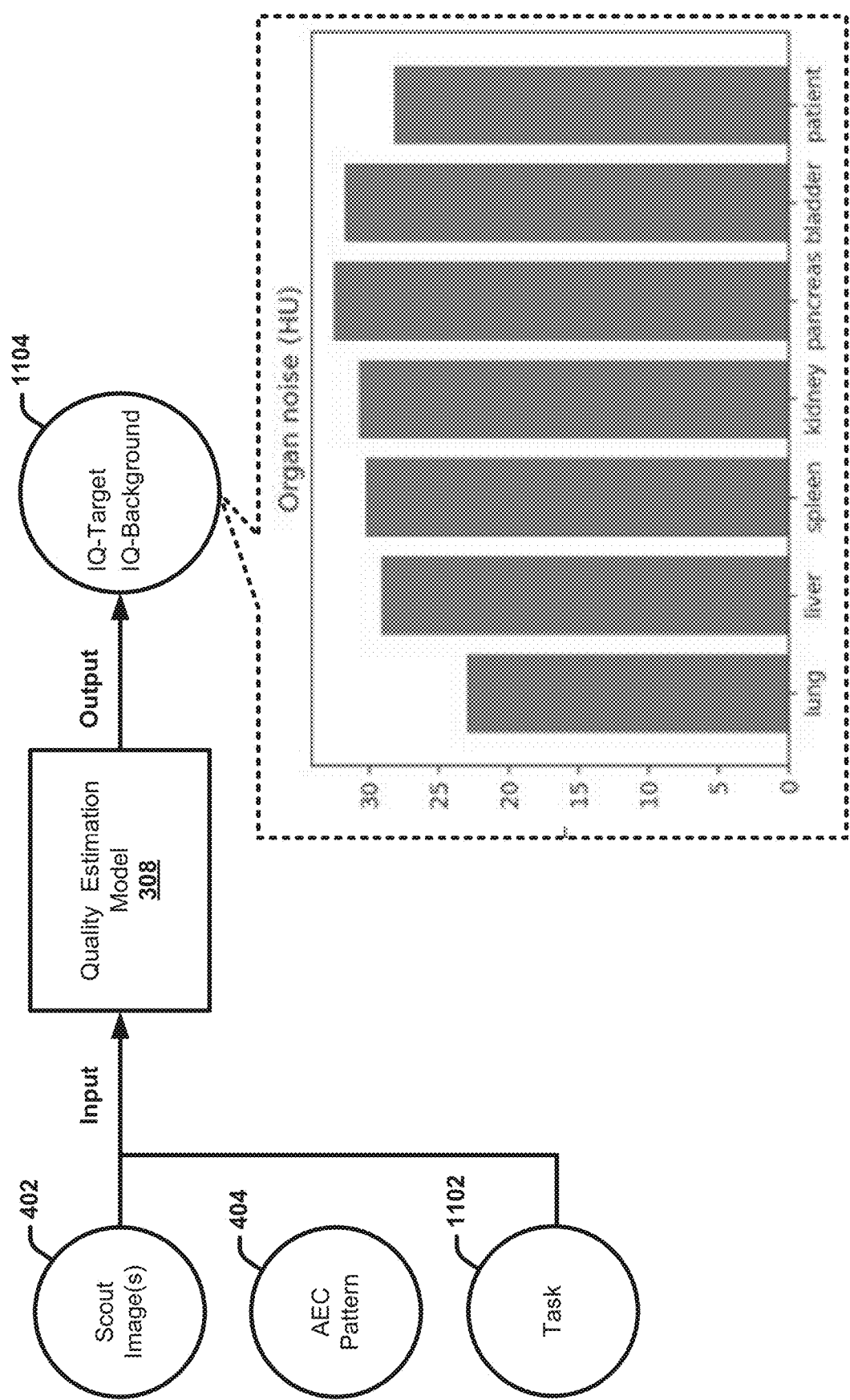
FIG. 11 presents an example quality estimation model in accordance with one or more embodiments of the disclosed subject matter.

FIG. 11 presents an example quality estimation model 308 in accordance with one or more embodiments of the disclosed subject matter. Repetitive description of like elements employed in respective embodiments is omitted for sake of brevity.

As illustrated in FIG. 11, the input to the image quality estimation model 308 can include the one or more scout images 402, a selected AEC pattern 404, and a selected task 1102. The task 1102 controls or otherwise defines the target and background region of the CT scan images. In various embodiments, the task 1102 can include a clinical task for which the CT scan is performed. In this regard depending on the clinical indication of the CT example, the particular organs, anatomical regions, etc., captured in the scan image that are of importance to clinical evaluation can vary. Additionally, or alternatively, the task 1102 can include a particular post-processing task that will be used to process the CT scan images, wherein the post-processing task is facilitated by higher levels of image quality in a target region relative to a background region. For example, in some implementations, the post-processing task involve processing the scan images using one or more automated medical image inferencing models adapted to perform automated image processing tasks such as but not limited to: disease/ condition classification, disease region segmentation, organ segmentation, disease quantification, disease/condition staging, risk prediction, temporal analysis, anomaly detection, anatomical feature characterization, medical image reconstruction, medical image enhancement, and the like.

In one or more embodiments, the task 1102 can be selected from amongst a define set of different tasks. In many example implementations, the target and background regions defined for the different tasks are based on the organs included in the anatomical ROI. For example, for a particular task, a target region could include one or more specific organs (e.g., the liver in association with detecting liver lesions), while other organs and anatomical features included in the ROI could be defined as background regions. However, the disclosed techniques are not limited to defining target and background regions in the scan images based on organs alone. In this regard, the target regions and background regions can be based on other defined anatomical landmarks, specific scan lines, specific prescription planes, specific points/locations in the scan images, and so on. The term target region is used herein to refer to the totality of the portion of the scan images considered a target region. In this regard, the "target region" can include two or more separate regions of the same CT scan image. Likewise, the "background region" can include two or more separate regions of the same CT scan image.

The output of the quality estimation model 308 includes one or more image quality measure or metrics that represent measures of expected image quality in the target region (IQ-target) and the background region (IQ-background) of the CT scan images to be acquired under the selected AEC pattern 404. In some embodiments, the measure of image quality can be based on image noise levels determined by segmenting target and background regions and differentiating between morphological variations and pixel differences due to photon noise. For example, in some example implementations, as shown in FIG. 11 the expected image quality can be provided a function of organ noise levels (measured in HU) and the overall noise level (e.g., patient). Additionally, or alternatively, the image quality measures can be based on one or more other factors, including but not limited to: mean noise, maximum noise, CNR, signal-to-noise ratio (SNR), noise power spectrum (NPS), detective quantum efficiency (DQE), detectability index. In the example shown in FIG. 11, the target regions and background regions are not explicitly identified but are understood to be based on the specific organs. For example, depending on the task 1102, the target region could include all of the organs or a subset (one or more) of the organs. Likewise, the background region could include a subset of the organs (e.g., one or more). Still in another example, the patient column could represent the background region and correspond to the mean noise level of the region of the scan images excluding the organs.

As with the organ dose estimation, in addition to the task 1102, the specific target and background regions can vary based on the particular organs included in the ROI of the patient scanned. In some implementations, the ROI can account for the entirety of the anatomical region represented in the scout images 402. In other implementations, the ROI can include a sub-region of the anatomical region depicted in the scout images. With these implementations, information defining the sub-region or scan range can also be provided as input with the scout images 402. As described in greater detail infra, in estimating target and background region image quality from the scout images 402, the quality estimation model 308 will implicitly learn the relevant target and background regions for each task and ROI, as well as how the different AEC patterns affect image quality in the CT volumes. As with the dose estimation models 304, in some embodiments, the quality estimation model 308 can be tailored to a specific anatomical ROI. With these embodiments, different quality estimation models 308 can be generated for different ROIs and selectively applied based on the ROI scanned.

The type or types of machine learning models used for the one or more quality estimation models 308 can vary. In some embodiments, the one or more quality estimation models 308 can include one or more deep learning models, such as CNNs, RESNET type models, and other neural network models with different types of pooling techniques. In some implementations, the quality estimation model 308 can employ a CNN architecture corresponding to that illustrated in FIG. 5. In another example, the one or more dose estimation models can employ a CNN architecture that includes, followed by a fully connected layer and regression layer that outputs the estimated quality metrics for the target and background regions. Other suitable types of the machine learning models can include but are not limited to, GAN, LSTMs, attention-based models, transformers, decision tree-based models, Bayesian network models, regression models and the like. These models may be trained using supervised, unsupervised and/or semi-supervised machine learning techniques.

Figure 12:
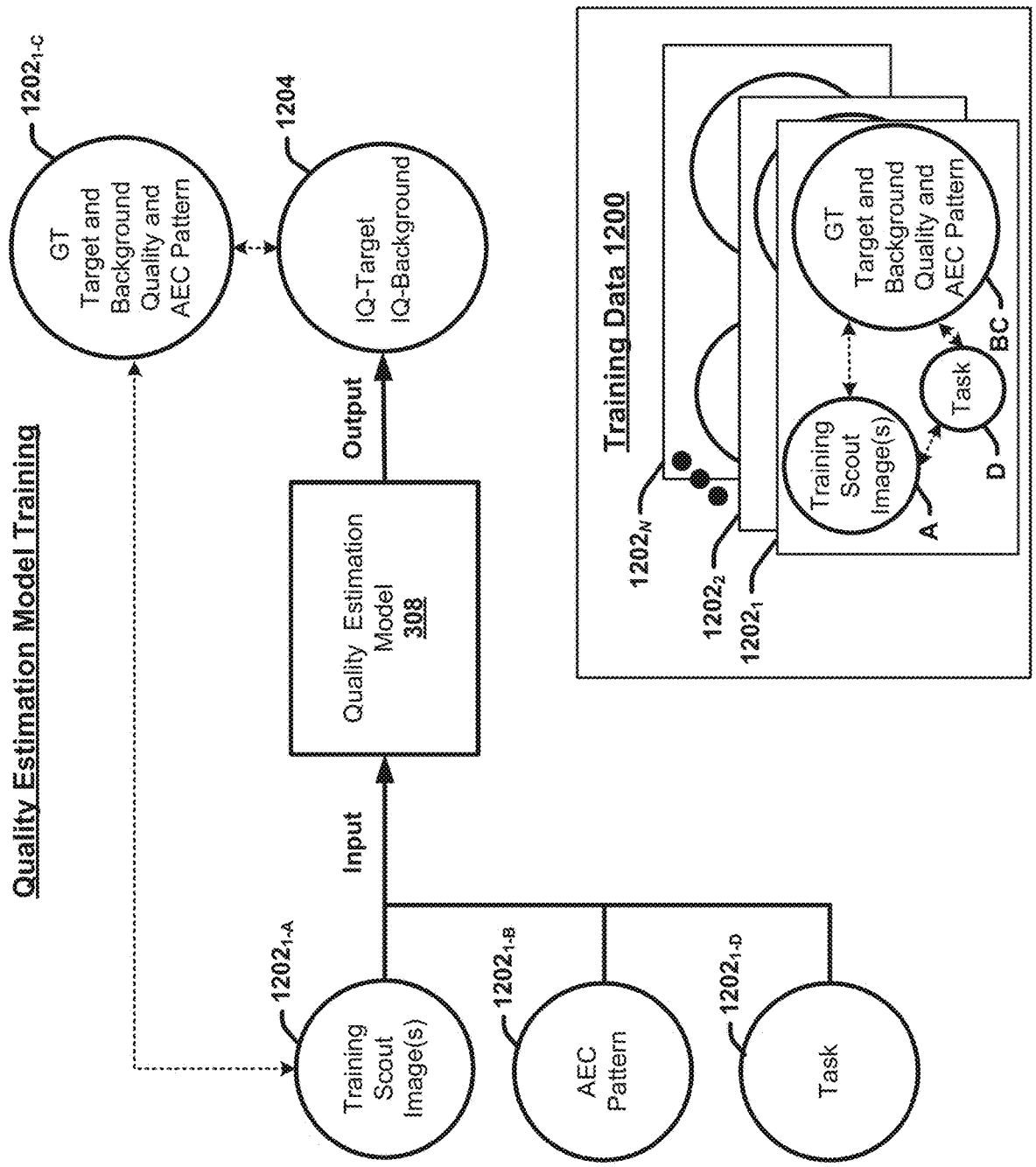
FIG. 12 illustrates quality estimation model training in accordance with one or more embodiments of the disclosed subject matter.

FIG. 12 illustrates quality estimation model training in accordance with one or more embodiments of the disclosed subject matter. As illustrated in FIG. 12, the quality estimation model training involves training the dose estimation model to predict the one or more measure of image quality in the target and background regions 1204 (e.g., IQ-target and IQ-background for a selected AEC pattern and task based on one or more scout images using ground truth CT generated target and background image quality measures. Techniques for generating these ground truth image quality metrics are discussed in greater detail below. With reference to FIGS. 3 and 12, in various embodiments, the training component 316 can perform the quality estimation model training illustrated in FIG. 12 using one or more supervised or semi-supervised machine learning training, testing and validation processes.

As illustrated in FIG. 12, the training data 1200 can include a plurality of different training data sets, respectively identified as $1202_{1-N}$. The number of training data sets N can vary. Each training data set includes four components respectively indicated with the letters A (component 1), B (component 2) and C (component 3) and D (component 4). In particular, the first component A includes one or more training scout images. These training scout images can include the same scout images used to train the dose estimation model 304 and/or additional or alternative scout images. In some implementations, the scout images can also include or otherwise be associated with information defining a scan range. The second component B includes a known/defined AEC pattern. The known/defined AEC pattern can also include the different AEC patterns used to train the dose estimation model 304. The third component C includes the GT target and background quality metrices determined for that AEC pattern. As discussed below, these GT quality metrics can also be generated using CT volume data paired with the training scout images, which can include the same scout image-CT volume data pairs (e.g., paired training scout images and CT volumes 801) used to generate the GT training data for the dose estimation model 304. The fourth component D includes a specific task, which controls/defines the relevant target and background regions.

In this regard, with respect to one example training data set $1202_1$, the input to the quality estimation model 308 includes the task $1202_{1-D}$, the AEC pattern $1202_{1-B}$ and the one or more training scout images $1201_{1-A}$. The quality estimation model 1204 is then trained to generate/estimate the target and background image quality metrics 1204 for AEC pattern $1202_{1-B}$ and task $1202_{1-D}$ the based on the training scout images $1202_{1-A}$ using the GT target and background quality metrics $1202_{1-C}$. The quality estimation model 308 will implicitly learn the relevant task and background regions for the task, as well as how AEC affects image quality in the CT volumes. In various implementations, the training component 316 can train the quality estimation model 308 to predict noise levels in these regions to within 1.0 HU, which will provide the level of accuracy needed for optimizing AEC.

It should be appreciated that the collective training data sets $1202_{1-N}$ represent scout images and paired CT volumes for different patients and different AEC pattern and task combinations. In this regard, the collective training data sets $1202_{1-N}$ can include groups of training data sets that include the same scout images for the same patient and task, yet paired with GT target and background quality metrics for different AEC patterns generated from the same paired CT volume data. Additionally, the collective training data sets $1202_{1-N}$ can include groups of training data sets that include the same scout images for the same patient and AEC pattern, yet paired with GT target and background quality metrics for different tasks generated from the same paired CT volume data. The collective training data sets $1202_{1-N}$ will also depict the same anatomical ROI when the quality estimation model 1204 is trained for a specific anatomical ROI (e.g., the abdomen for example).

Figure 13:
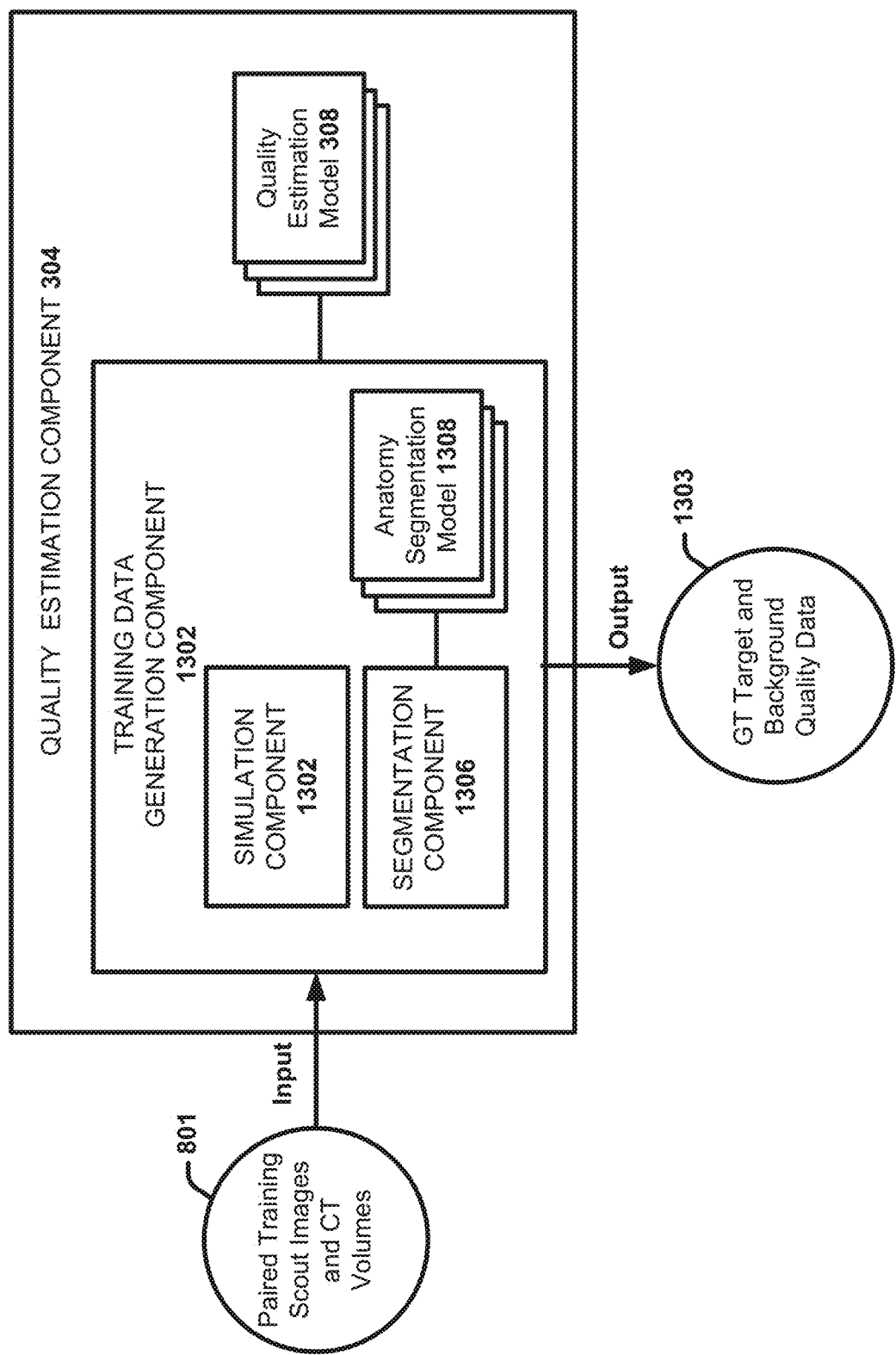
FIG. 13 illustrates an example quality estimation component in accordance with one or more embodiments of the disclosed subject matter.

FIG. 13 presents an example quality dose estimation component 306 in accordance with one or more embodiments of the disclosed subject matter. Repetitive description of like elements employed in respective embodiments is omitted for sake of brevity.

In some embodiments, the quality estimation component 306 can include training data generation component 1302 to generate the GT target and background quality data 1303 for training the one or more quality estimation models 308. In this regard, the GT target and background quality data 1303 can correspond to GT target and background quality training data included in training data 1200 for different AEC and task combinations. As illustrated in FIG. 8, in some embodiments, the training data generation component 1302 can employ the same paired training scout images and CT volumes 801 used to generate the GT organ dose data 803 to generate the GT target and background quality data 1303. The paired training scout images and CT volumes 801 can depict the same anatomical ROI in implementations in which the quality estimation model 308 is trained for a particular anatomical ROI.

Figure 14:
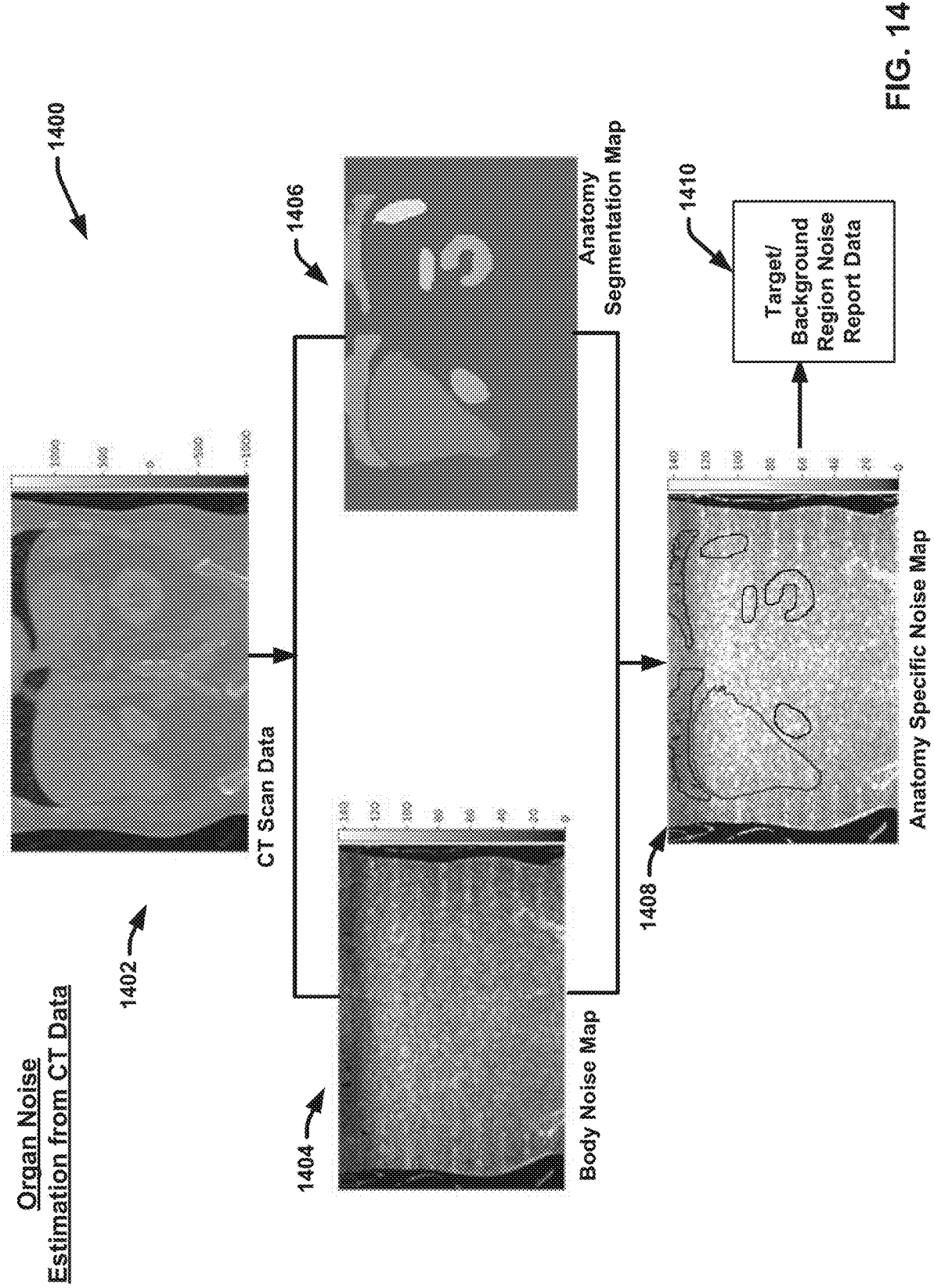
FIG. 14 illustrates an example pipeline for organ noise estimation from CT data in accordance with one or more embodiments of the disclosed subject matter.

In one or more embodiments, the training data generation component 1302 can generate the GT target and background quality data 1303 using noise maps generated from the CT volume data corresponding to the body dose maps (e.g., body dose map 606). These noise maps can reflect different noise distributions in expected CT scan images generated under different AEC patterns. These noise maps can further be segmented into target and background regions and the respective noise levels can be mapped to the corresponding target and background regions, as illustrated in FIG. 14. To facilitate this end, the training data generation component 1302 can include simulation component 1302, segmentation component 1306 and one or more anatomy segmentation models 1308.

In this regard, FIG. 14 illustrates an example pipeline 1400 for organ noise estimation from CT data in accordance with one or more embodiments of the disclosed subject matter. Pipeline 1400 starts with a CT scan data 1402 corresponding to one or more CT scan slices that make up a CT scan volume. With reference to FIGS. 13 and 14, in one or more embodiments, the simulation component 1302 can employ the CT scan data 1402 to compute a body noise map 1404 that represents the distribution of noise in the CT scan data 1402 at a specific AEC pattern. The segmentation component 1306 can further segment the CT scan data 1402 using one or more anatomy segmentation models 1308 to facilitate identifying the target regions and background regions in the CT scan data 1402 as illustrated by the anatomy segmentation map 1406. For example, in various embodiments, the one or more anatomy segmentation models 1308 can include or correspond to the one or more organ segmentation models (e.g., organ segmentation models 808) used to perform the organ segmentation of the CT scan data for the organ dose mapping. With these embodiments, the segmented anatomy segmentation map can segment the organs anatomical features in the CT scan data 1402. Additionally, or alternatively, the one or more anatomy segmentation models 1406 can include segmentation models that are adapted to segment a variety of different anatomical landmarks or features in the CT scan data 1402 (e.g., other than organs). For example, the other anatomical landmarks or features can include bone, soft tissue, lesions, artifacts, scan planes, specific locations or points in the CT scan data 1402 and so on.

The training data generation component 1302 can further combine the anatomy segmentation map 1406 with the body noise map 1404 to obtain an anatomy specific noise map 1408. The anatomy specific noise map 1408 provides a mapping of the body noise levels to the segmented anatomical regions identified in the anatomy segmentation map. In this regard, using the body noise map and the anatomy segmentation map 1406, the training data generation component 1302 can determine the mean noise levels associated with each of the segmented anatomical regions, including the specific landmarks and the background area exploiting the specific landmarks. From this mapping, the training data generation component 1302 can generate target and background noise report data 1410 that identifies the mean noise level associated the target region and the background region, wherein the mean noise levels reflect the specific AEC pattern. Because the target and background regions can vary based on task, the target and background noise report data can also vary by task. For example, in some implementations in which the segmented anatomical regions include organs in the ROI, the target and background region noise report data 1410 may identify the mean noise levels for each of the segmented organs and the mean noise level for the region of the CT scan data excluding the organs. With these implementations, the target region may include all of the organs or a subset of the organs, and the background region may include the region excluding all or the subset of the organs, depending on the task. In other embodiments, the target/background region noise report data 1410 can include the specific noise levels for each anatomy segmented landmark/feature represented in the anatomy segmentation map 1406 and the mean noise level for the remaining region (e.g., excluding the anatomy segmented regions). From this data, the target and background regions can be selectively defined based on task under the same AEC pattern. It should be appreciated that the same anatomy segmentation map 1406 can be mapped to different body noise maps generated from the same CT scan data 1402 for different AEC patterns. In this regard, as the body noise maps change depending on the AEC pattern modeled, the noise values for the selected target and background regions as defined based on the anatomy segmentation map 1406 will also vary.

Figure 15:
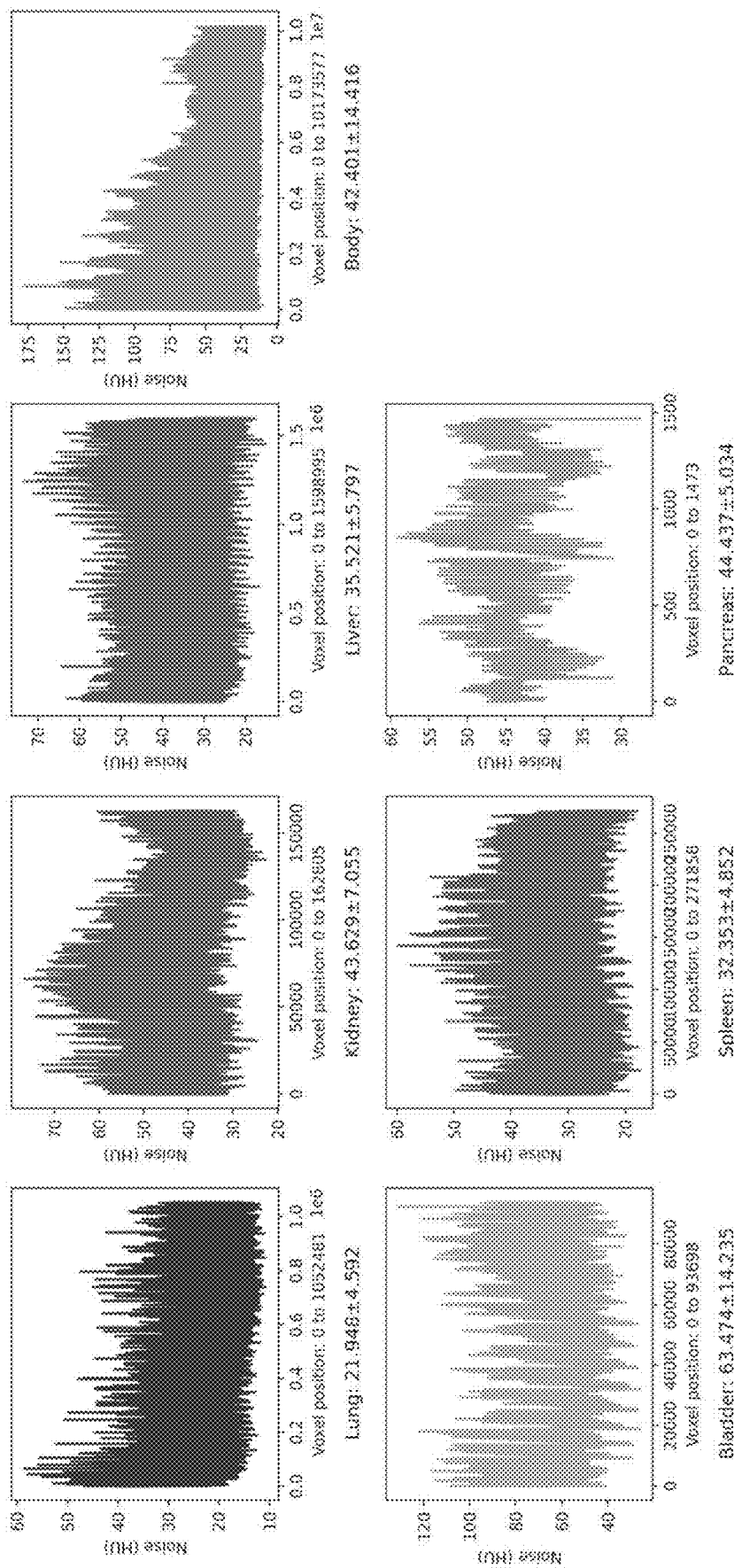
FIG. 15 illustrates organ specific noise report information generated from CT in accordance with one or more embodiments of the disclosed subject matter.

FIG. 15 illustrates example organ specific noise report information generated from CT data using the techniques described above. The CT organ noise report data illustrated in FIG. 15 provides example noise report data that can be included in the target and background region noise report data 1410. In accordance with this example, organ anatomy segmentation was used to segment the relevant organs in the ROI using the same organ segmentation models 808 used to generate the organ dose report data shown in FIG. 7. In this regard, the mean noise levels were calculated for each of the individual organs under a specific AEC pattern. In this example, the CT organ noise dose report data is demonstrated for the body (e.g., which can reflect the total image quality and/or the region excluding the organs) and six different organs associated with an abdomen scan, including the lungs, kidney, liver, bladder, spleen and pancreas. The organ dose report data plots the noise levels (e.g., in HU) for different voxel positions and provides the mean noise level across all voxel positions for each component (e.g., the organs and body).

Figure 16:
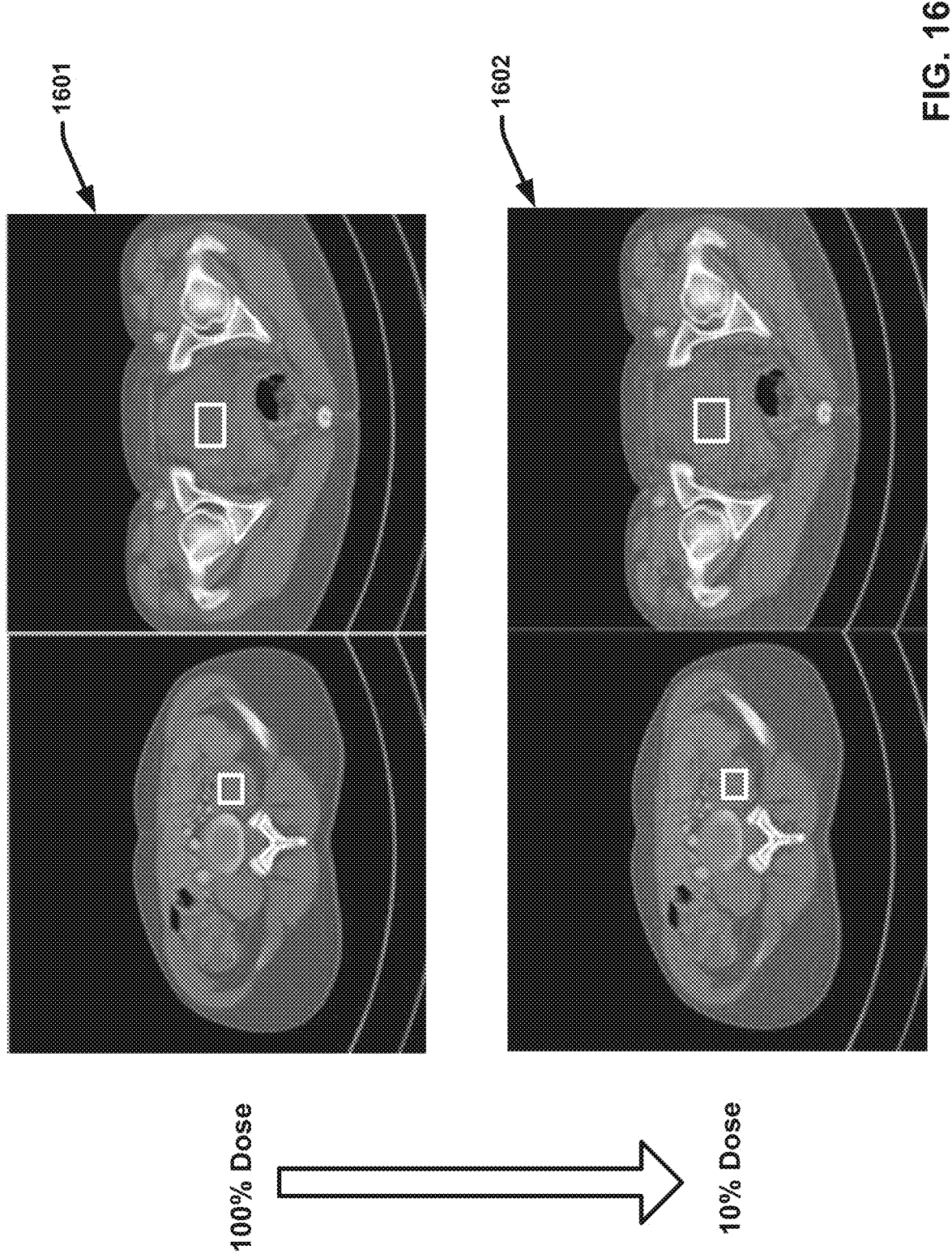
FIG. 16 illustrates example CT scan images generated from CT volume data under different radiation dosage percentages in accordance with one or more embodiments of the disclosed subject matter.

With reference again to FIGS. 13 and 14, the techniques employed by the simulation component 1302 to generate the body noise maps 1404 for different AEC patterns from the CT volume data can vary. In some embodiments, the simulation component 1302 can generate the body noise maps 1404 from the CT volume data under different AEC patterns representing different TCMs and/or other different AEC parameter values using simulation techniques. In this regard, in association with performance of a CT scan with TCM, as the tube current is modulated, image quality in the projections vary, which influence the image quality in the reconstructed scan images. In some embodiments, to establish the GT target and background quality data 1303, the simulation component 1302 can determine image quality metrics (e.g., noise and/or other image quality metrics) for different AEC patterns by simulating projections at different tube current levels (and thus different dosage level) using the CT volume and generating corresponding reconstructed scan images. For each projection, the simulation component 1302 can insert noise corresponding to the tube current and spatial variation of the beam (e.g., due to bowtie), accounting for quantum and electronic noise, as illustrated in FIG. 16. This requires an accurate model of the CT scanner, including its source spectrum and detector response.

In this regard, FIG. 16 illustrates example CT scan images generated from CT volume data under different radiation dose percentages. The upper set of scan images 1601 corresponds to scan images captured at 100% dose, while the lower set of scan images 1602 illustrate scan images generated at a 10% dose. In various embodiments, the simulation component 1302 can generate different sets of reconstructed scan images from the raw CT volume data at different dose levels ranging from 100% to 10% by inserting noise into the raw CT data. In this example, the upper set of scan images 1601 corresponds to reconstructed scan images without noise and the lower set of scan images 1602 corresponds to reconstructed scan images simulated without 90% noise. As can be seen by comparison of the respective scan image sets, the high dose images 1601 at 100% dose and no added noise have better visualization of tissues due to lower noise relative to the low dose images 1602 with added noise. The scan images in both sets are respectively marked with boxes to indicate example target regions of interest.

In accordance with these embodiments, the simulation component 1302 can generate the reconstructed scan images from the simulated projections with and without added noise as illustrated in FIG. 16. The simulation component 1302 can generate multiple noise realizations at different dose levels (e.g., 100% dose, 75% dose, 50% dose, 25% dose, 5% dose, etc.) to better estimate image noise levels. For filtered back projection reconstructions, the noise should be highly realistic due to its quasi-linear nature. The simulation component 1302 can also employ iterative reconstruction (e.g., ASIR) and deep learning image reconstruction (DLIR) techniques to facilitate generating the simulated dose levels.

Figure 17:
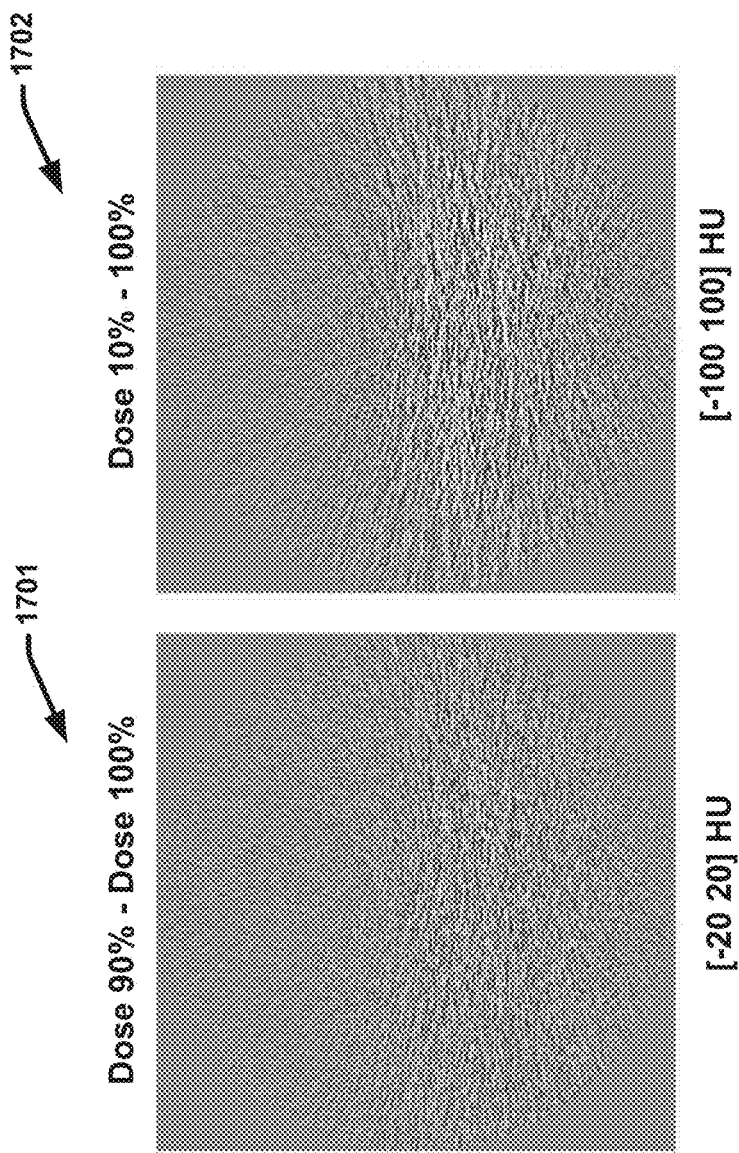
FIG. 17 illustrates generation of a differential images from simulated noise images in accordance with one or more embodiments of the disclosed subject matter.

The simulation component 1302 can further determine the expected image noise distribution values for a scan image generated under a specific AEC pattern and/or at a specific dose level associated with the AEC pattern based on the difference between the noise projections with and without added noise, as illustrated in FIG. 17.

In this regard, FIG. 17 illustrates generation of differential images from a high dose image at 100% dose and a simulated low-dose image. The first differential image 1701 depicts a differential noise image generated based on the difference between the high dose image at 100% dose and another scan image simulated at 90% dose. The second differential image 1702 depicts another differential noise image generated based on the difference between the high dose image at 100% dose and another scan image simulated at 10% dose. The differential images show the added noise, but not the original noise at full dose.

In one or more embodiments, the simulation component 1302 can estimate noise levels from the differential images (e.g., first differential image 1701, second differential image 1702, and the like), using empirical curve fitting to estimate the standard deviation at an arbitrary dose. To facilitate this end, the simulation component 1302 can first calculate standard deviation (stdev) maps of difference images at two simulated doses (which helps capture behavior across the dose range), in accordance with Equation 8.

$\sigma_{Diff1}$=the stdev map of difference images $Im_{D1}$-$Im_{1.0}$; and $\sigma_{Diff2}$=the stdev map of difference images $Im_{D2}$-$Im_{1.0}$ Equation 8.

The simulation component 1302 can then estimate the standard deviation of the arbitrary dose D≤1 in accordance with Equation 9.

$\sigma_D = \sigma_{Diff1} \times (a_{11}/D + a_{12}\sqrt{D} + a_{13}) + \sigma_{Diff2} \times (a_{21}/D + a_{22}\sqrt{D} + a_{23})$ Equation 9.

Figure 18:
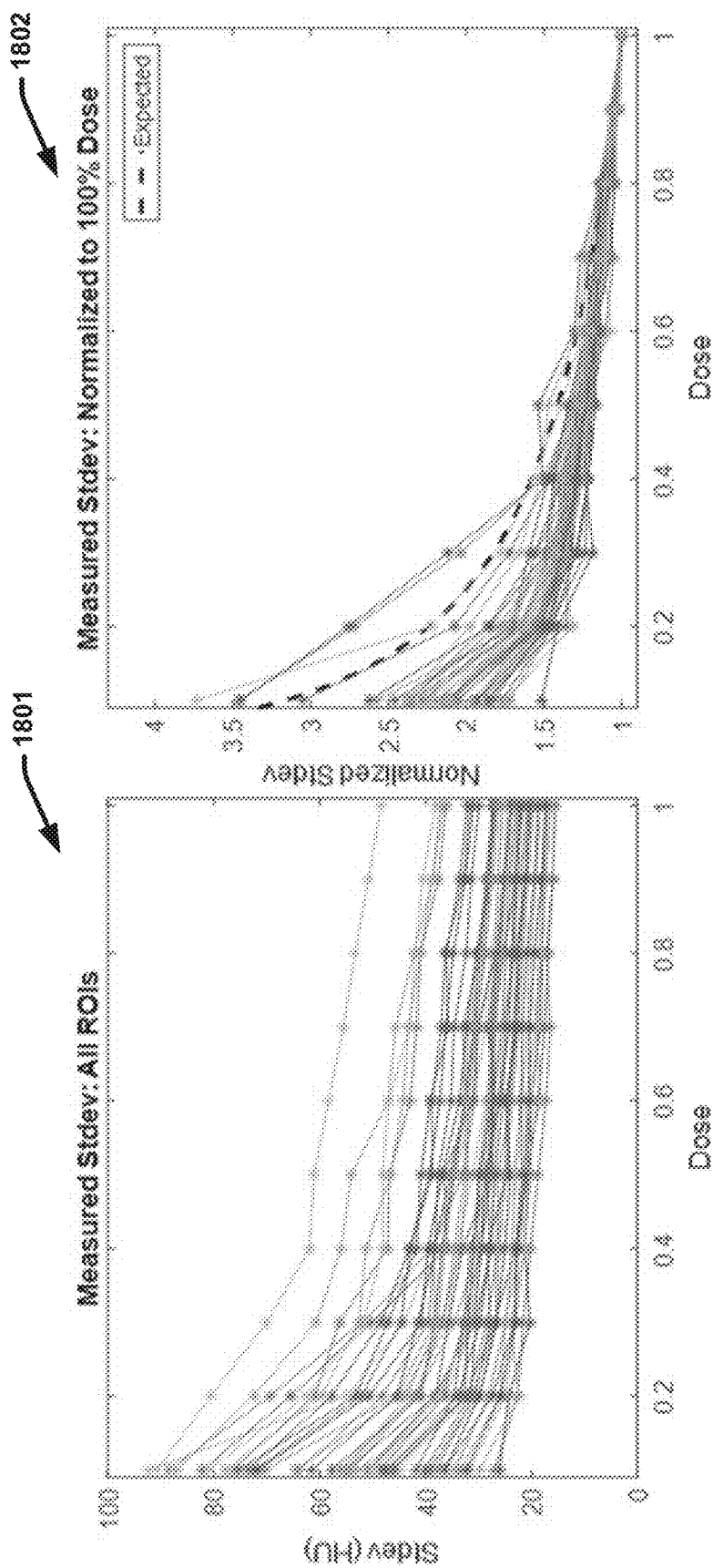
FIG. 18 provides graphs illustrating measuring noise in uniform regions across simulated doses in accordance with one or more embodiments of the disclosed subject matter.

FIG. 18 provides graphs illustrating measured noise in uniform regions across all simulated doses in accordance with the techniques described above. Graph 1801 plots the noise levels (e.g., measured as a function of the standard deviation of the difference images) of a plurality of different image regions as a function of dose, wherein each line corresponds to a different region. Graph 1802 plots the normalized or arbitrary noise levels normalized to 100% dose.

Figure 19:
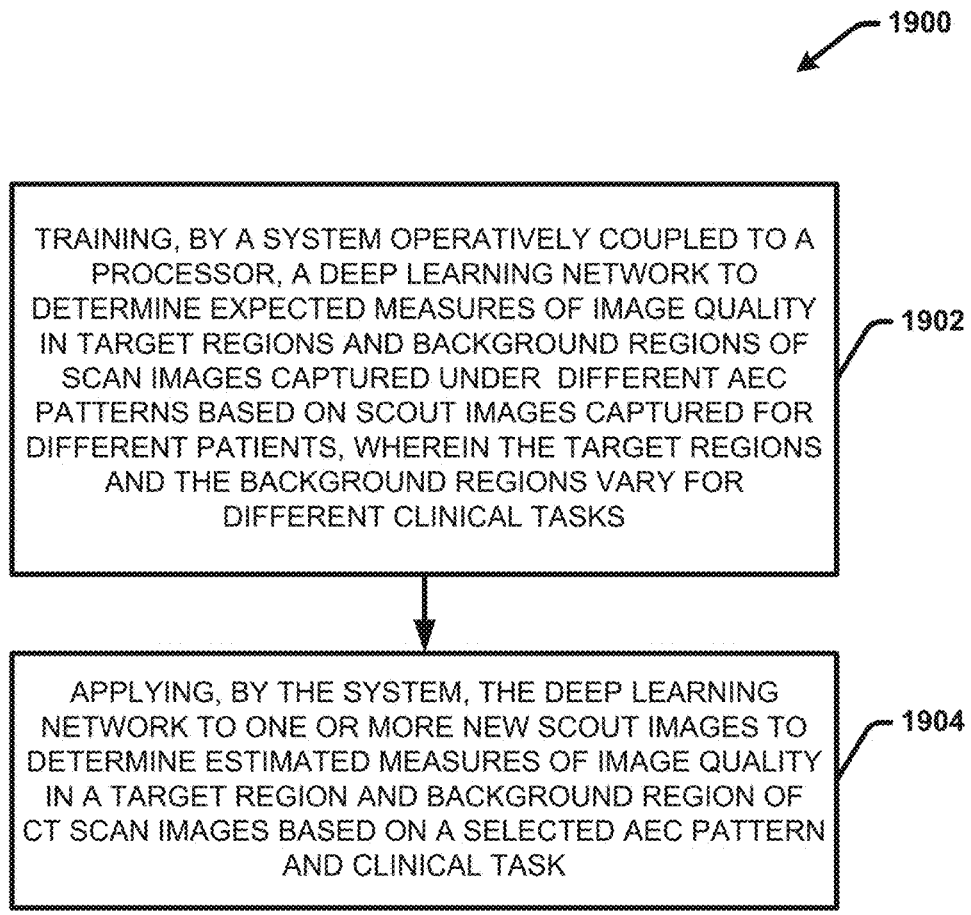
FIG. 19 presents a high-level flow diagram of an example process for estimating measures of image quality in target and background regions under a selected AEC pattern based on one or more scout images in accordance with one or more embodiments of the disclosed subject matter.

FIG. 19 presents a high-level flow diagram of an example process 1900 for estimating measures of image quality in target and background regions under a selected AEC pattern based on one or more scout images in accordance with one or more embodiments of the disclosed subject matter. Process 1900 provides an example process that can be performed by computing system 300 using reception component 314, training component 316, quality estimation component 306 and inferencing component 318. Repetitive description of like elements employed in respective embodiments is omitted for sake of brevity.

In accordance with process 1900, at 1902, a system operatively coupled to a processor (e.g., system 300 or the like) can train (e.g., by the quality estimation component 306 using training component 316 in accordance with FIG. 12), a deep learning network (e.g., a quality estimation model 306), to determine expected measure of image quality (e.g., noise levels and/or one or more other image quality metrics) in target regions and background regions of scan images captured under different AEC patterns based on scout images captured for different patients, wherein the target regions and the background regions for different clinical tasks. In some embodiments, prior to performing the training at 1902, process 1900 can also include generating the GT training and background image quality metrics from matching CT volumes for the scout images using simulated image quality maps under the different AEC patterns and subsequent anatomy segmentation of the 3D dose maps into the target and background regions for the different clinical tasks.

At 1904, once the deep learning network (i.e., the quality estimation model 308) has been trained, tested and validated, the system can apply (e.g., by the quality estimation component 306 using inferencing component 318) the deep learning network to one or more new scout images captured of the anatomical region of a patient to determine estimated measure of image quality in a target region and background region of CT scan images based on a selected AEC pattern and clinical task.

AEC Optimization

The previous sections provide deep learning techniques that enable separately estimating patient specific organ doses under different AEC settings and estimating how the different organ doses and AEC settings impact expected image quality in the scan images for a specific task. Using these two separate deep learning networks (i.e., the dose estimation model 304 and the quality estimation model 308) the following description leverages these two networks to facilitate determining the optimal AEC settings for a particular patient and task while balancing the competing objectives of minimizing radiation dose exposure to the patient while achieving a desired level of image quality in the target region needed for clinical evaluation. To facilitate this end, the following AEC optimization techniques employ the dose estimation model 304 and the quality estimation model 308 to determine optimal AEC settings for different patients and different tasks based on their training scout images that deliver the requested image quality at the minimum dose, formulating the optimal AEC as an optimization problem. These optimal AEC settings are then used as ground truth exemplars to build an end-to-end model that maps the scout and task to the optimal AEC in real-time.

Figure 20:
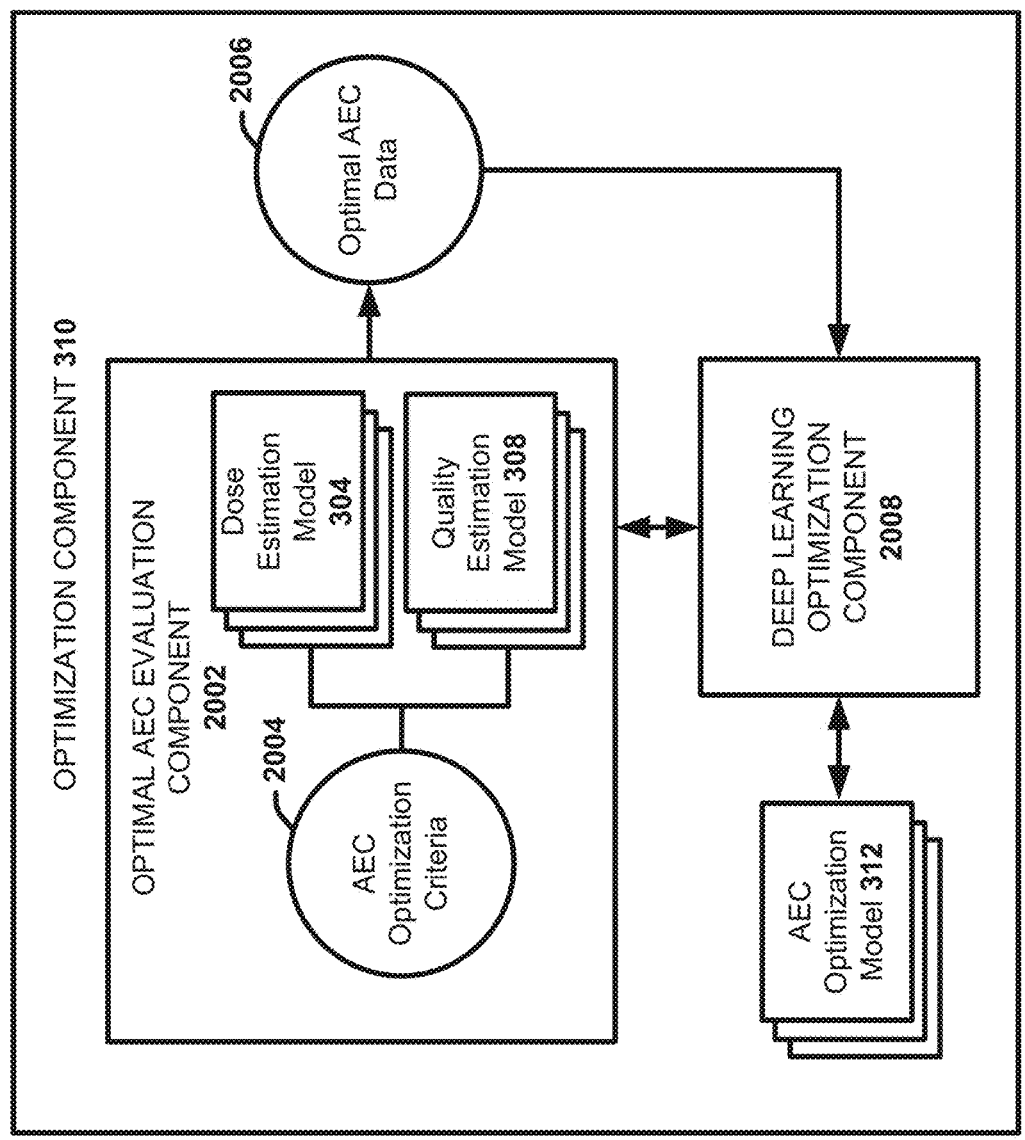
FIG. 20 illustrates an example optimization component in accordance with one or more embodiments of the disclosed subject matter.

With reference to FIG. 20 illustrated is an example optimization component 310 in accordance with one or more embodiments of the disclosed subject matter. Repetitive description of like elements employed in respective embodiments is omitted for sake of brevity.

The optimization component 310 can include an optimal AEC evaluation component 2002 and a deep learning optimization component 2008. The optimal AEC evaluation component 2002 can employ the trained dose estimation model(s) 304 and the trained quality estimation model(s) 308 to determine and evaluate how different AEC settings affect organ dose and target and background region image quality directly from one or more scout images. The optimal AEC evaluation component 2002 can further employ one or more combinatorial optimization techniques to iteratively evaluate how different AEC patterns impact organ dose and image quality in the target and background regions to converge on an optimal AEC for a specific patient and task (wherein the task defines/controls the target and background regions) that best achieves and/or balances (e.g., in accordance with a defined weighting schemed) defined AEC optimization criteria 2004.

In various embodiments, the AEC optimization criteria 2004 can model AEC as an optimization problem that balances the competing objectives of dose minimization and quality maximization. In particular, the AEC optimization criteria 2004 can provide an optimization function that defines the optimal AEC a function of optimization criteria for the organ doses and the image quality in the target region, wherein the optimization criteria is based on minimizing organ dose and maximizing image quality. For example, in some implementations, the optimization function can be modeled as follows: given the scouts and a task, maximize image quality in the target region for a fixed dose subject to system constraints (i.e., the feasible space of AEC). In another implementations, the optimization function can be modeled as follows: given the scouts and a task, minimize organ dose for a fixed image quality in the target region, subject to system constraints (i.e., the feasible space of AEC). Still in other embodiments, the optimization criteria of the optimization function can be based on defined thresholds and/or ranges for maximum and minimum organ doses and target/background region image quality.

In some embodiments, the optimal AEC evaluation component 2002 can employ a derivative-free optimization function such as covariance matrix adaptation evolution strategy (CMA-ES) to determine the optimal AEC for a specific scout image/task combination. Such optimization methods employ repeat evaluations of the objective function (dose and image quality), as illustrated in FIG. 21.

Figure 21:
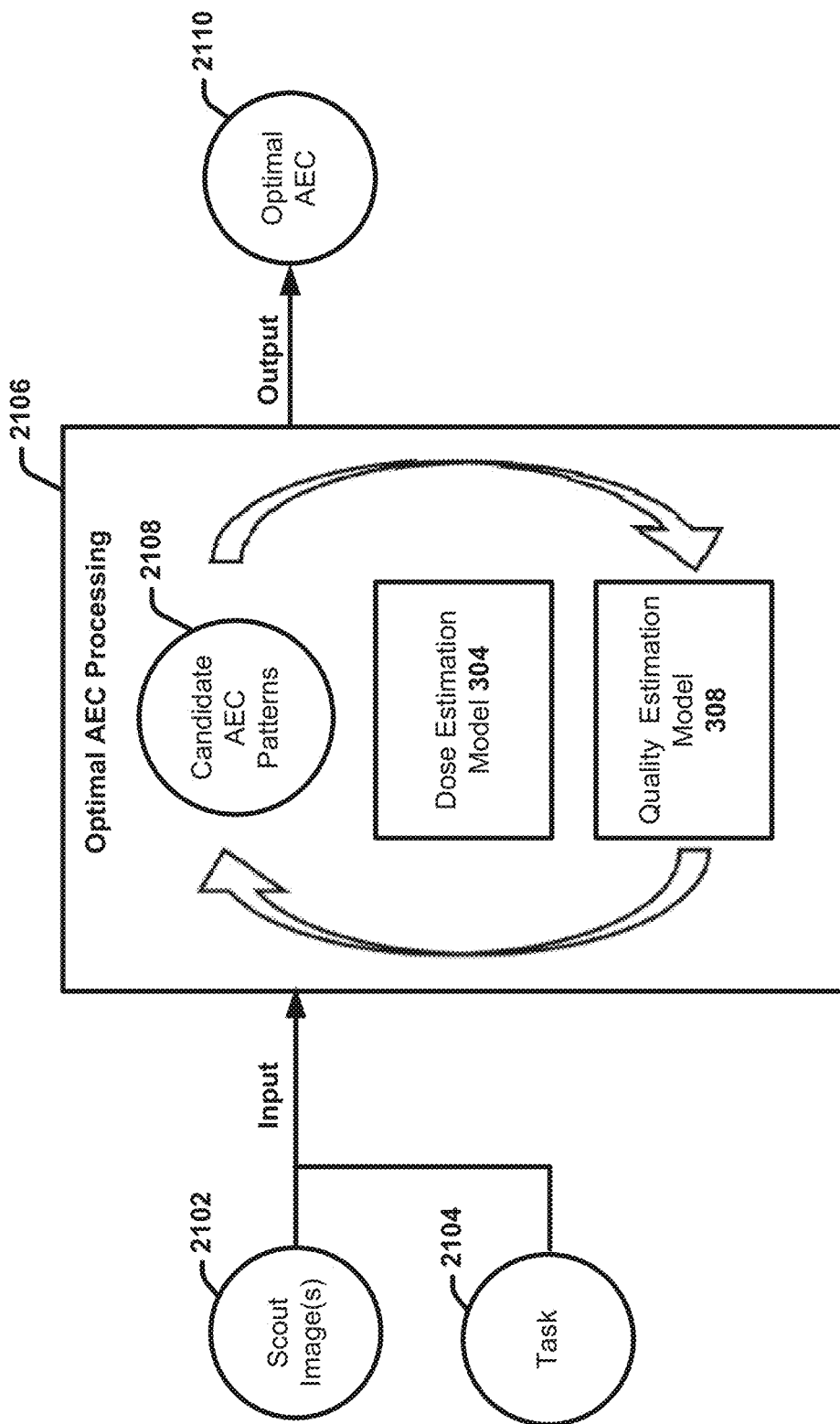
FIG. 21 illustrates optimal AEC processing to determine an optimal AEC based on one or more scout images and a specific task in accordance with one or more embodiments of the disclosed subject matter.

In this regard, FIG. 21 illustrates optimal AEC processing 2106 that can be performed by the optimal AEC evaluation component 2002 to determine an optimal AEC 2110 based on one or more scout images 2102 and a specific task 2104. The scout images 2102 can include one or more scout images (e.g., single perspective scout images, lateral and frontal scout images, etc.) captured of an anatomical ROI of a patient. For example, the scout images 2102 can correspond to scout images 102, scout images 402, training scout images $902_{1-A}$, training scout images $1202_{1-A}$, or the like. The task 2104 can include a selected task from amongst the defined set of tasks for which the quality estimation model 308 was trained.

In accordance with this embodiment, the optimal AEC processing 2106 involve iteratively applying the dose estimation model 304 and the quality estimation model 308 to the scout images under different candidate AEC patterns 2108 and determining the expected organ doses and target and background image quality metrics under each of the candidate AEC patterns 2108. While each evaluation of the deep learning models is expected to be sub-second, the overall optimization processing time may range from second to several minutes depending on the processing speed of the processing hardware used for the many evaluations of the objective function. The optimal AEC evaluation component 2002 then selects the optimal AEC 2110 from amongst the candidate AEC patterns that best achieves the optimization criteria for the organ doses and target/background region image quality. In this regard, assuming the optimization criteria is based on maximum fixed dose, the optimal AEC evaluation component 2002 can find the best AEC pattern that achieves the highest image quality in the target region at the maximum fixed dose. In other implementation, the optimization criteria can be tailored to balance dose and target region image quality based on defined weightings for the organ dose and the target region image quality. With these implementations, the optimal AEC 2110 may include an AEC that provides a high level of image quality in the target region (e.g., but not the highest), while also providing low organ doses (e.g., but not the lowest).

In some embodiments, the optimal AEC processing 2106 illustrated in FIG. 21 can be used in association with performance of an actual CT scan prior to the capture of the high-resolution scan images (e.g., while the patient is on the scanning table). For example, with reference again to FIG. 1, the optimal AEC processing 2106 can correspond to the AI model processing at 104. With these implementations, the optimal AEC processing 2106 can be used to determine the optimal AEC for the patient and task for an actual imaging procedure in the clinical workflow.

In other embodiments, the scout images 2102 can correspond to training scout images included in a set of training scout images. For example, the set of training scout images can include the same training scout images used to train the dose estimation model 304 and/or the quality estimation model (e.g., the training scout images included in training data 900 and/or training data 1200). In other implementations, the training scout images used as input for the optimal AEC processing 2106 can include new scout images. Either way, with these embodiments, the optimal AEC processing 2106 can be applied to each of the training scout images to determine optimal AEC patterns for each training scout image and task combination. These optimal AEC patterns can then be used as the GT exemplars to train and develop an end-to-end model that takes scouts and a task as input and directly outputs the optimal AEC.

With reference again to FIG. 20, in the embodiment shown, this end-to-end model can include one or more AEC optimization models 312. With these embodiments, the optimal AEC data 2006 can correspond to the GT optimal AEC patterns for the different scout image/task combinations. In this regard, the deep learning optimization component 2008 can employ the training component 316 to train one or more AEC optimization models 312 to take one or more scout images and selected task as input and directly output the optimal AEC. The training data will consist of the predetermined optimal AECs for different scout image/task combinations using the optimal AEC evaluation component 2002 and the techniques described with reference to FIG. 21. In this regard, while optimal AEC evaluation component 2002 explicitly estimates dose and image quality for each AEC candidate, the AEC optimization model 312 can be trained to implicitly model these in its prediction of the optimal AEC. This direct prediction should run in real-time in inference mode.

The type or types of machine learning models used for the one or more AEC optimization model 312 can vary. In some embodiments, the one or more AEC optimization model 312 can vary can include one or more deep learning models, such as CNNs, RESNET type models, and other neural network models with different types of pooling techniques. Other suitable types of the machine learning models can include but are not limited to, GAN, LSTMs, attention-based models, transformers, decision tree-based models, Bayesian network models, regression models and the like. These models may be trained using supervised, unsupervised and/or semi-supervised machine learning techniques. The number of AEC optimization models 312 can also vary. In this regard, in some embodiment, a plurality of different AEC optimization models 312 may be trained and tailored to different anatomical ROIs synonymous with the corresponding dose estimation models 304 and quality estimation models 308. In other embodiments, universal AEC optimization model 312 can be developed that can be applied to any anatomical ROI.

Figure 22:
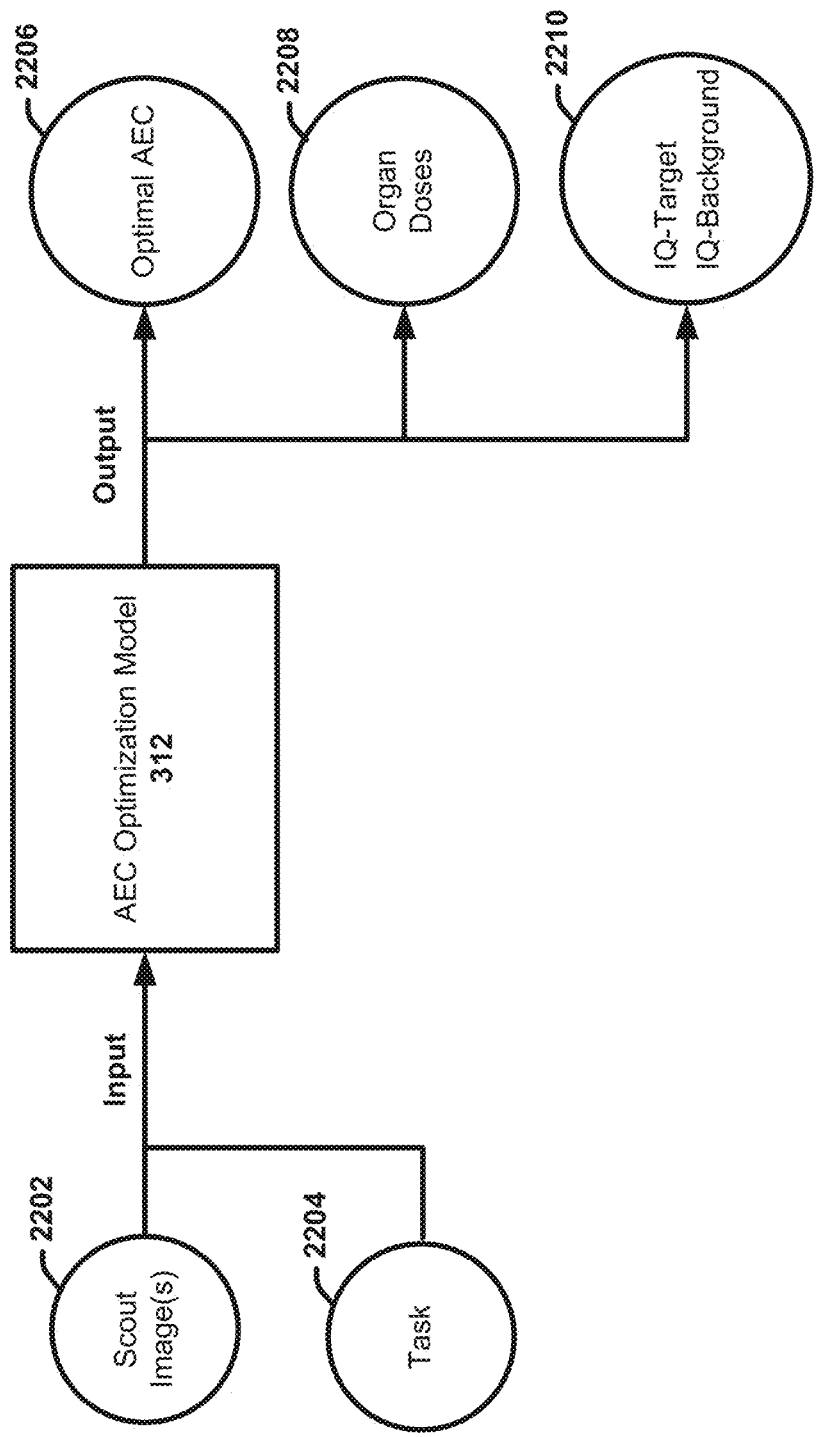
FIG. 22 illustrates an example AEC optimization model in accordance with one or more embodiments of the disclosed subject matter.

FIG. 22 illustrates an example AEC optimization model 312 once trained in accordance with one or more embodiments. In various embodiments, the learning optimization component 2008 (and/or the inferencing component 318) can apply the AEC optimization model 312 in the clinical workflow to provide real-time AEC optimization for CT imaging scans. For example, with reference again to FIG. 1, the AI model processing at 104 can correspond to application of the AEC optimization model 312 as illustrated in FIG. 22. In this regard, once trained, the input to the AEC optimization model 312 can include a one or more scout images 2202 captured of an anatomical region of a patient and a selected task 2204. The output of the AEC optimization model 312 includes the optimal AEC 2206.

In some embodiments, the AEC optimization model 312 can also be configured to generate the expected organ doses 2208 and the expected target and background image quality 2210 for the optimal AEC pattern 2206. Additionally, or alternatively, once the optimal AEC 2206 has been generated by the AEC optimization model 312, the dose estimation model 304 and/or the quality estimation model 308 can then be separately applied to the scout images 2202 using the optimal AEC 2206 as the selected AEC pattern to determine the organ doses 2208 and the expected target and background image quality 2210 for the optimal AEC pattern 2206. Therefore, as the user selects the task or modifies other acquisition parameters, the resulting impact on dose and IQ will dynamically be made available, as well as an optimized AEC ready to scan the patient. The delivered AEC and predicted dose and IQ can be included in the scan report.

Figure 23:
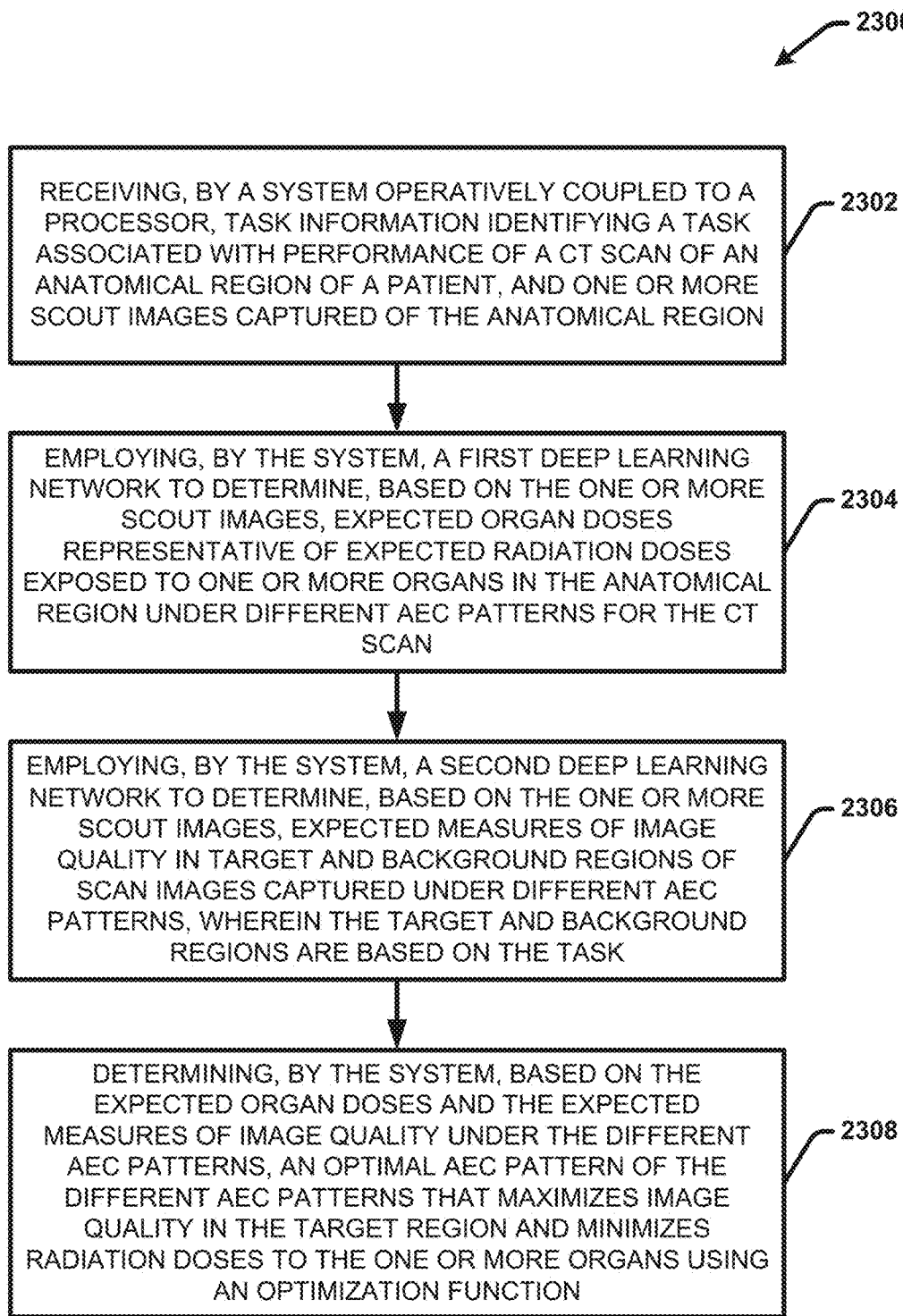
FIG. 23 presents a high-level flow diagram of an example computer-implemented process for determining an optimal AEC in accordance with one or more embodiments of the disclosed subject matter.

FIG. 23 presents a high-level flow diagram of an example computer-implemented process 2300 for determining an optimal AEC in accordance with one or more embodiments of the disclosed subject matter. Process 2300 provides an example process that for performance by the optimal AEC evaluation component 2002 in accordance with various embodiments described herein. Repetitive description of like elements employed in respective embodiments is omitted for sake of brevity.

In accordance with process 2300, at 2302, a system, operatively coupled to a processor (e.g., system 300 and the like), receives (e.g., via reception component 314) task information identifying a task associated with performance of a CT scan of an anatomical region of a patient, and one or more scout images captured of the anatomical region. For example, in some implementations, the scout images and task information can be received in association with performance of an actual CT scan prior to the capture of the high-resolution scan images (e.g., while the patient is on the scanning table). With these implementations, process 2300 can be used to determine the optimal AEC for the patient and task for an actual imaging procedure in the clinical workflow. In other implementations, the scout images can correspond to training scout images included in a set of training scout images. With these implementations, process 2300 can be applied to each of the training scout images to determine optimal AEC patterns for each training and task combination. These optimal AEC patterns can be used by the deep learning optimization component 2008 (and the training component 316) to train and develop the one or more AEC optimization models 312.

At 2304, the system employs a first deep learning network (e.g., dose estimation model 304) to determine based on the one or more scout images (e.g., using optimal AEC evaluation component 2002), expected organ doses representative of expected radiation doses exposed to (or absorbed by) one or more organs in the anatomical region under different AEC patterns for the CT scan. At 2306, the system employs a second deep learning network (e.g., quality estimation model 308) to determine, based on the one or more scout images (e.g., using optimal AEC evaluation component 2002), expected measures of image quality in target and background regions of scan images captured under the different AEC patterns, wherein the target and background regions are based on the task. At 2308, the system determines (e.g., using optimal AEC evaluation component 2002), based on the expected organ doses and the expected measures of image quality under the different AEC patterns, an optimal AEC pattern of the different AEC patterns that maximizes image quality in the target region and minimizes the radiation doses to the one or more organs using an optimization function (e.g., provided by the AEC optimization criteria 2004).

Figure 24:
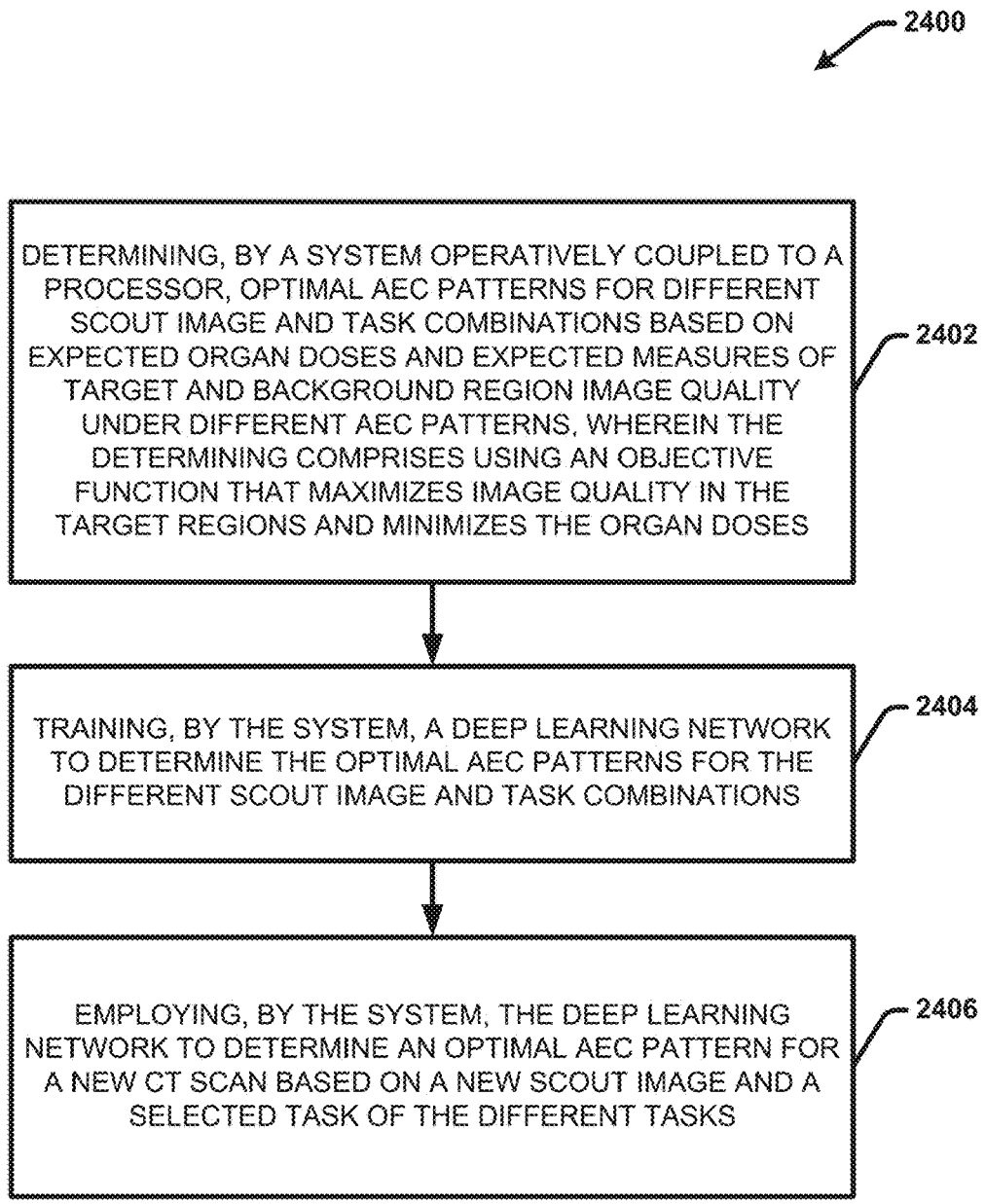
FIG. 24 presents a high-level flow diagram of an example computer-implemented process for determining an optimal AEC in accordance with one or more embodiments of the disclosed subject matter.

FIG. 24 presents a high-level flow diagram of another example computer-implemented process 2400 for determining an optimal AEC in accordance with one or more embodiments of the disclosed subject matter. Process 2400 provides an example process for performance by the optimal AEC evaluation component 2002 and the deep learning optimization component 2008 in accordance with various embodiments described herein. Repetitive description of like elements employed in respective embodiments is omitted for sake of brevity.

In accordance with process 2400, at 2402, a system, operatively coupled to a processor (e.g., system 300 and the like), determines (e.g., using optimal AEC evaluation component 2002), optimal AEC patterns for different scout image and task combinations based on expected organ doses and expected measure of target and background region image quality under different AEC patterns, wherein the determining comprises using an objective function that maximizes image quality in the target regions and minimizes the organ doses. At 2404, the system trains a deep learning network (e.g., an AEC optimization model 312) to determine the optimal AEC patterns for the different scour image and task combinations (e.g., via the deep learning optimization component 2008 and the training component 316). At 2406, the system employs the deep learning network to determine an optimal AEC pattern for a new CT scan based on a new scout image (or images) and a selected task of the different tasks (e.g., via the deep learning optimization component 2008 and the inferencing component 318).

Figure 25:
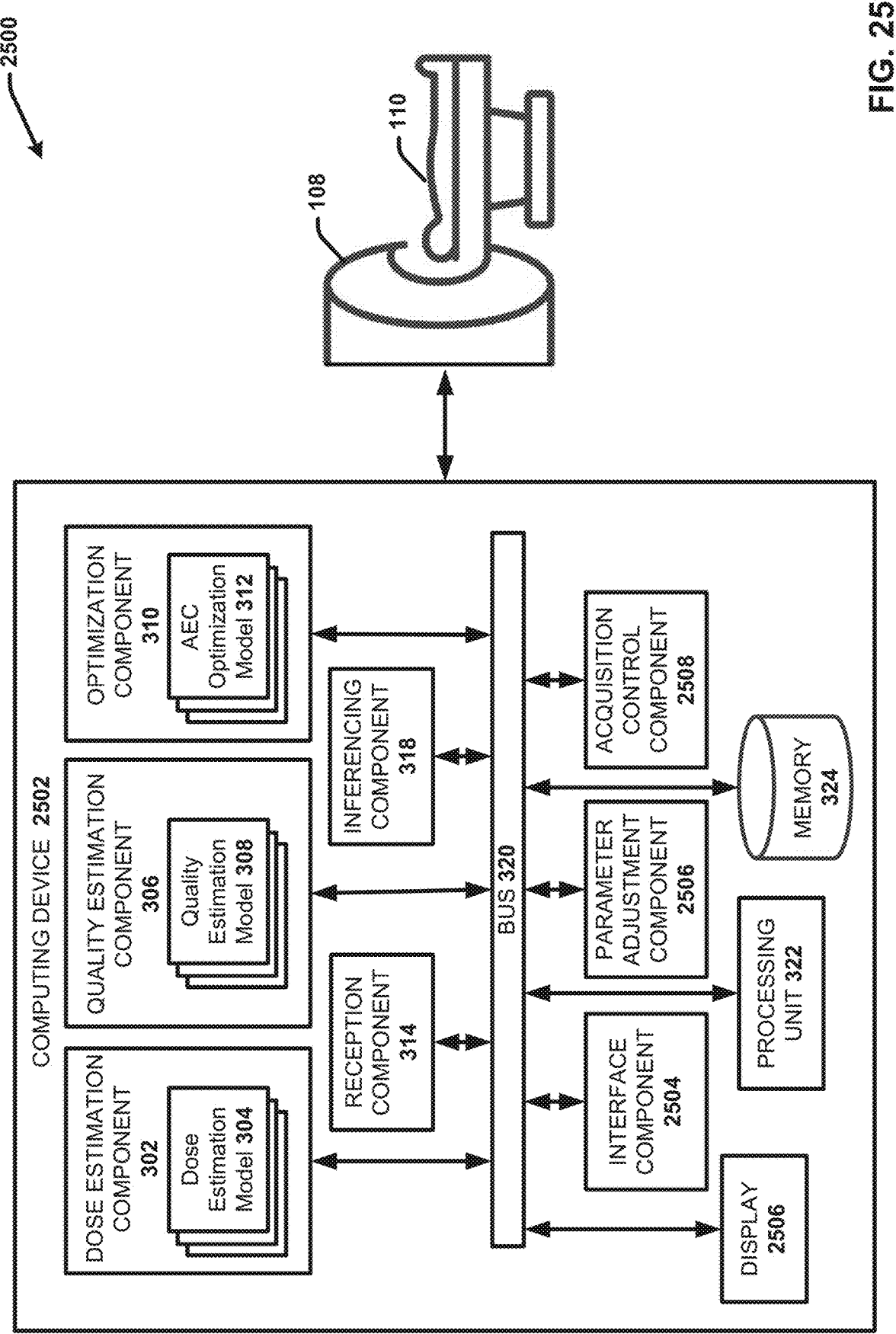
FIG. 25 presents another example computing system that facilitates tailoring AEC setting to specific patient anatomies and clinical tasks in accordance with one or more embodiments of the disclosed subject matter.

FIG. 25 presents another example computing system 2500 that facilitates tailoring AEC setting to specific patient anatomies and clinical tasks in accordance with one or more embodiments of the disclosed subject matter. Computing system 2500 includes a computing device 2502 and a CT scanner 108. The computing device 2502 can be operatively and/or communicatively coupled to the CT scanner 108 and provide for controlling one or more operations of the CT scanner 108. The computing device 2502 can include same or similar components as computing system 300 with the addition of interface component 2504, parameter adjustment component 2506, acquisition control component 2508 and display 2506. Repetitive description of like elements employed in respective embodiments is omitted for sake of brevity.

In accordance with system 2500, the training component 316 has be excluded from the computing device 2502 to indicate an implementation in which the training and development of the one or more dose estimation models 304, the one or more quality estimation models 208 and the one or more AEC optimization models 312 has be completed. In this regard, system 2500 provides an example run-time environment wherein one or more of these models can be executed in real-time by the inferencing component 318 in association performing an actual CT scan on a patient 110 in accordance with process 100. With these embodiments, the computing device 2502 can correspond to a computing device employed by the CT scanner operating technician (or another suitable entity).

For example, prior to the performance of the CT scan and the acquisition of high-resolution CT scan images, the reception component 314 can receive one or more low resolution scout images of the anatomical ROI of the patient to be scanned. The reception component 314 can also receive information selecting/defining the relevant task for the performance of the CT scan, which controls/defines the relevant target and background regions for the high-resolution scan images. The inferencing component 318 can further apply the one or more AEC optimization models 312 to the scout images under the selected task to generate an optimal AEC pattern (e.g., optimal AEC settings) for the patient and task. In some embodiments, the inferencing component 318 can also apply the one or more dose estimation models 304 to the scout images under the optimal AEC pattern to generate the estimated organ doses that will be absorbed under the optimal AEC pattern. The inferencing component 318 can also apply the one or more quality estimation models 308 to the scout images under the optimal AEC pattern and task to generate the estimated measure of target and background region image quality. Information identifying the optimal AEC pattern, the estimated organ doses and/or the measure of target and background region image quality can be presented to the operating technician via the display. The acquisition control component 2508 can further automatically configure the CT scanner to perform the CT scan (e.g., the high-resolution CT scanning process) using the optimal AEC pattern.

To facilitate this end, the interface component 2504 can provide an interactive graphical user interface (GUI) that can be presented to the operating technician via the display 2506 in association with performing AEC and configuring and controlling the CT acquisition by the CT scanner. The interactive GUI can facilitates receiving user input selecting/defining the task (and/or adjusting AEC optimization criteria), executing the one or more models, presenting the model outputs, and controlling one or more operations of the CT scanner 108. For example, the GUI can provide controls for receiving user input identifying one or more parameters of the CT acquisitions, receiving the scout images and defining/selecting the task for the CT exam. In some embodiments, the GUI can include an optimal AEC control that automatically generates the optimal AEC for the patient and task based on the scout images using the technique described herein. The acquisition control component 2508 can further configure the CT scanner to perform the CT exam using the optimal AEC pattern either automatically and/or in response to user input provided by the operating technician requesting usage of the optimal AEC pattern by the CT scanner 108. For example, the acquisition control component can be operatively coupled to the imaging device that performs the CT scan (e.g., the CT scanner 108) and control performance of the CT scan by the imaging device based on the optimal AEC pattern.

The parameter adjustment component 2506 can also provide additional tools (e.g., accessed via the GUI) that allow the operator to provide input adjusting one or more parameters of the optimal AEC and/or providing optimization criteria for the optimal AEC (e.g., a desired image quality level and/or a desired organ dose distribution). For example, the parameter adjustment component 2506 can facilitate receiving user input adjusting one or more parameters of the optimal AEC, resulting in a modified AEC pattern. Based on reception of the user input, the inferencing component 318 can re-apply the one or more dose estimation models 304 and the one or more quality estimation models 308 to the scout images to determine updated expected radiation doses to the one or more organs and updated measures of expected image quality in the target/background regions under the modified AEC pattern in real-time. The modified AEC can then be configured for the CT scanner via the acquisition control component 2508. In another example, the parameter adjustment component 2506 can facilitate receiving user input defining the optimization criteria for the optimal AEC pattern. In particular, the parameter adjustment component 2506 can provide adjustment controls that allow the operating technician to provide input identifying at least one of, a desired image quality for the target and/or background regions and a desired radiation dose to the one or more organs. Based on reception of the user input, the optimization component 310 can determine a modified AEC pattern that achieves the desired image quality and the desired radiation dose. For example, in some implementations, the optimization component 310 can employ the optimal AEC evaluation component 2002 to re-evaluate the optimal ACE using the modified ACE optimization criteria in association with re-applying (e.g., by the inferencing component 318) the dose estimation model 304 and the quality estimation model 308 to the scout images. Additionally, or alternatively, the one or more AEC optimization models 312 can include a model configured to generate an optimal AEC pattern under user defined AEC optimization criteria and a selected task based on the scout images. Therefore, as the user selects the task or modifies other acquisition parameters, the resulting impact on dose and IQ will dynamically be made available, as well as an optimized AEC ready to scan the patient. In addition to configuring and controlling the CT scanner to perform the CT acquisition using the optimal AEC, information identifying the AEC used, the predicted dose and the predicted target/background IQ can be included in the scan report.

Figure 26:
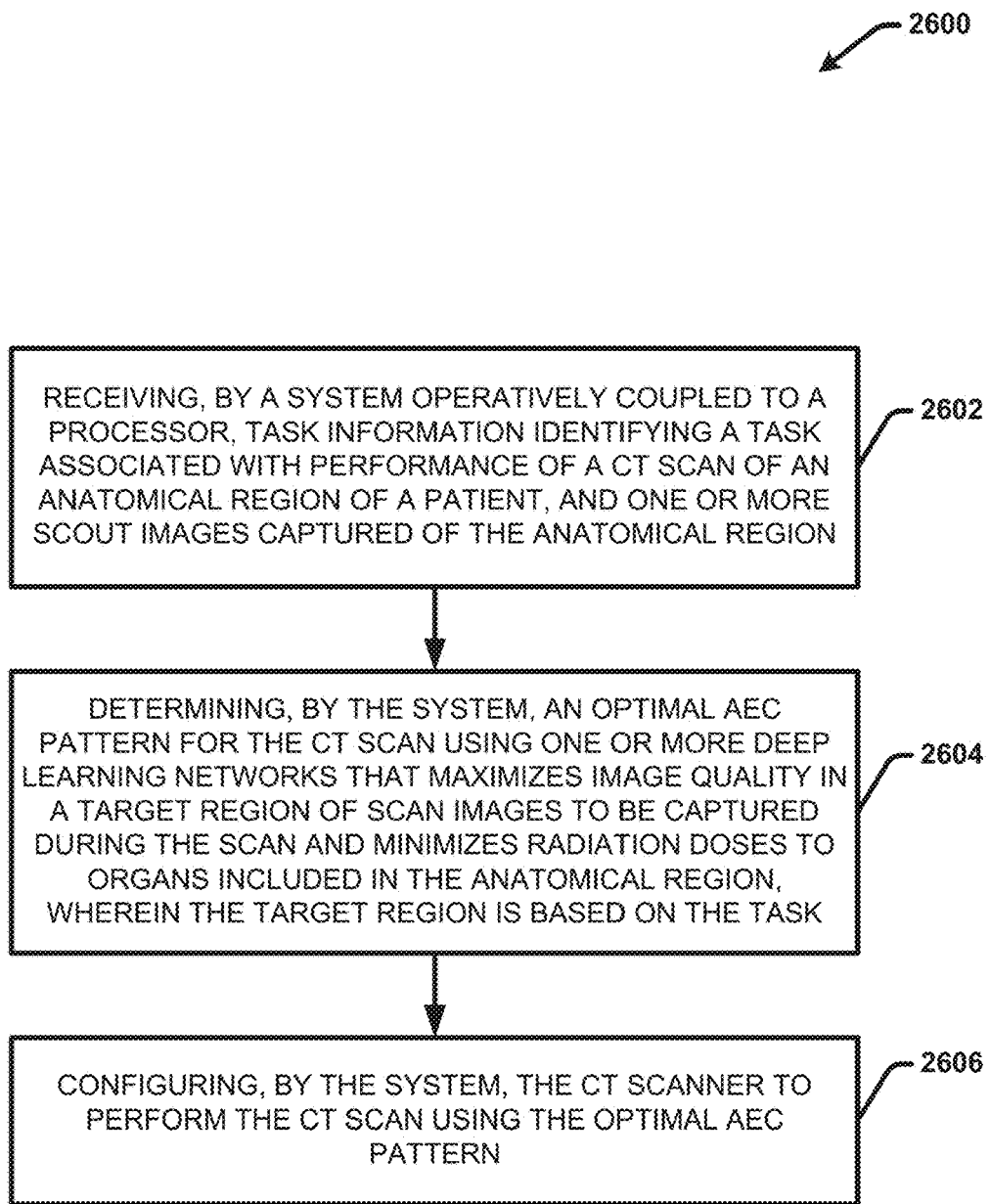
FIG. 26 presents a high-level flow diagram of an example computer-implemented process for performing a CT exam using optimal AEC in accordance with one or more embodiments of the disclosed subject matter.

FIG. 26 presents a high-level flow diagram of another example computer-implemented process for performing a CT exam using optimal AEC in accordance with one or more embodiments of the disclosed subject matter. Repetitive description of like elements employed in respective embodiments is omitted for sake of brevity.

In accordance with process 2600, at 2602, a system, operatively coupled to a processor (e.g., system 2500 and the like) receives (e.g., via reception component 314) task information identifying a task associated with performance of a CT scan of an anatomical region of a patient, and one or more scout images captured of the anatomical region. For example, in some implementations, the scout images and task information can be received in association with performance of an actual CT scan prior to the capture of the high-resolution scan images (e.g., while the patient is on the scanning table). With these implementations, process 2600 can be used to determine the optimal AEC for the patient and task for an actual imaging procedure in the clinical workflow and the scout images can be received directly from the CT scanner 108 (e.g., via the acquisition control component 2508).

At 2604, the system determines (e.g., using optimization component 310) an optimal AEC pattern for the CT scan using one or more deep learning networks (e.g., one or more optimization models 312, one or more dose estimation models 304 and/or one or more quality estimation models 308) that maximizes image quality in a target region of scan images to be captured during the scan and minimizes radiation doses to organs included in the anatomical region, wherein the target region is based on the task. At 2606, the system configures the CT scanner (e.g., CT scanner 108) to perform the CT scan using the optimal AEC pattern.

Example Operating Environment

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, procedural programming languages, such as the "C" programming language or similar programming languages, and machine-learning programming languages such as like CUDA, Python, Tensorflow, PyTorch, and the like. The computer readable program instructions can execute entirely on the user's computer, partly on the user's computer, as a stand-alone software package, partly on the user's computer and partly on a remote computer or entirely on the remote computer or server using suitable processing hardware. In the latter scenario, the remote computer can be connected to the user's computer through any type of network, including a local area network (LAN) or a wide area network (WAN), or the connection can be made to an external computer (for example, through the Internet using an Internet Service Provider). In various embodiments involving machine-learning programming instructions, the processing hardware can include one or more graphics processing units (GPUs), central processing units (CPUs), and the like. For example, one or more of the disclosed machine-learning models (e.g., the one or more dose estimation models 304, the one or more quality estimation models 308, the one or more optimization models 312, the one or more organ segmentation models 808, and the one or more anatomy segmentation models 1308) may be written in a suitable machine-learning programming language and executed via one or more GPUs, CPUs or combinations thereof. In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 27, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 27:
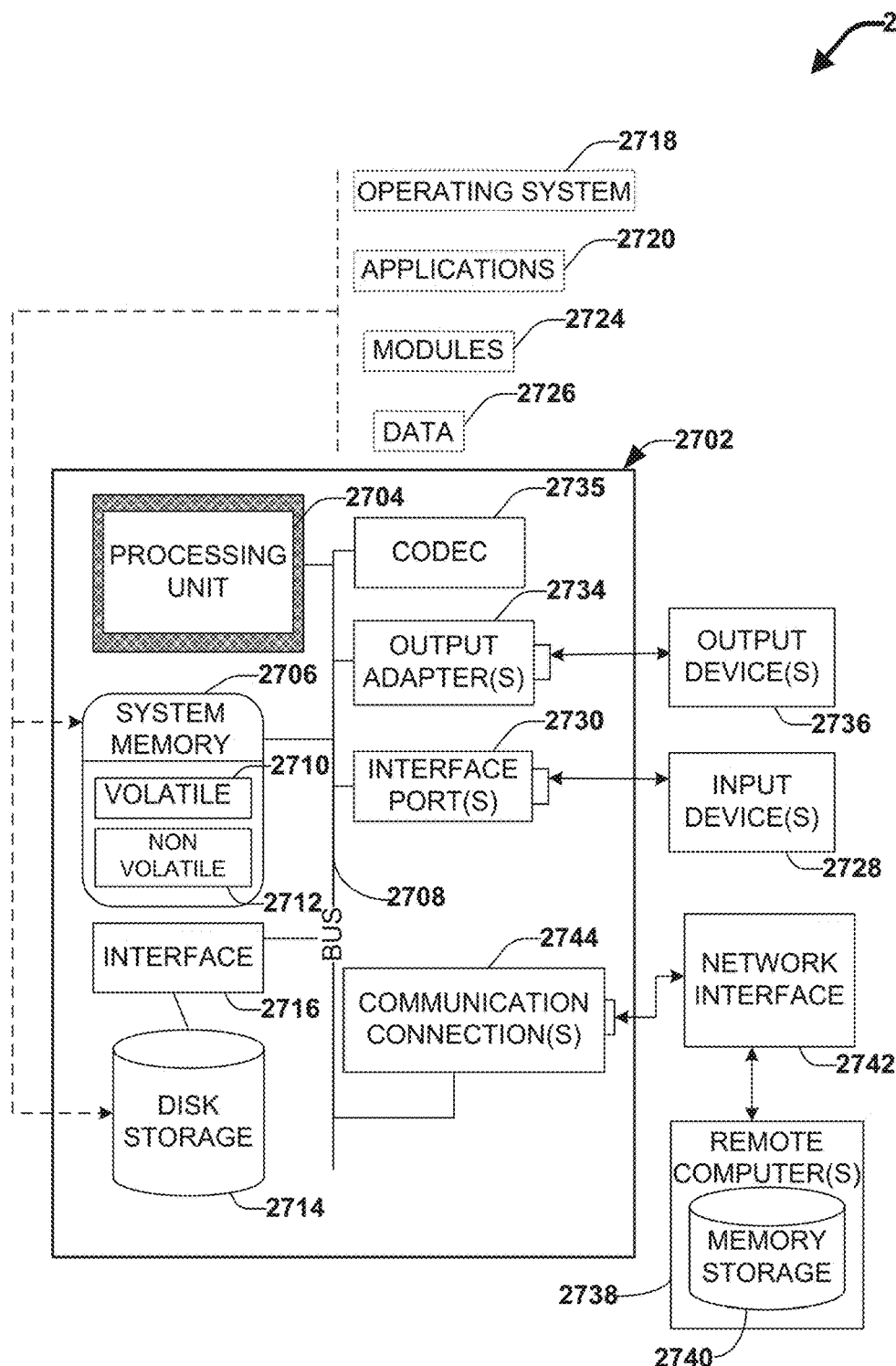
FIG. 27 illustrates a block diagram of an example, non-limiting operating environment in which one or more embodiments described herein can be facilitated.

With reference to FIG. 27, an example environment 2700 for implementing various aspects of the claimed subject matter includes a computer 2702. The computer 2702 includes a processing unit 2704, a system memory 2706, a codec 2735, and a system bus 2708. The system bus 2708 couples system components including, but not limited to, the system memory 2706 to the processing unit 2704. The processing unit 2704 can be any of various available processors. Dual microprocessors, one or more GPUs, CPUs, and other multiprocessor architectures also can be employed as the processing unit 2704.

The system bus 2708 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 2706 includes volatile memory 2710 and non-volatile memory 2712, which can employ one or more of the disclosed memory architectures, in various embodiments. The basic input/output system (BIOS), containing the basic routines to transfer information between elements within the computer 2702, such as during start-up, is stored in non-volatile memory 2712. In addition, according to present innovations, codec 2735 can include at least one of an encoder or decoder, wherein the at least one of an encoder or decoder can consist of hardware, software, or a combination of hardware and software. Although, codec 2735 is depicted as a separate component, codec 2735 can be contained within non-volatile memory 2712. By way of illustration, and not limitation, non-volatile memory 2712 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 2712 can employ one or more of the disclosed memory devices, in at least some embodiments. Moreover, non-volatile memory 2712 can be computer memory (e.g., physically integrated with computer 2702 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 2710 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 2702 can also include removable/non-removable, volatile/non-volatile computer storage medium. FIG. 27 illustrates, for example, disk storage 2714. Disk storage 2714 includes, but is not limited to, devices like a magnetic disk drive, solid state disk (SSD), flash memory card, or memory stick. In addition, disk storage 2714 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 2714 to the system bus 2708, a removable or non-removable interface is typically used, such as interface 2716. It is appreciated that disk storage 2714 can store information related to a user. Such information might be stored at or provided to a server or to an application running on a user device. In one embodiment, the user can be notified (e.g., by way of output device(s) 2736) of the types of information that are stored to disk storage 2714 or transmitted to the server or application. The user can be provided the opportunity to opt-in or opt-out of having such information collected or shared with the server or application (e.g., by way of input from input device(s) 2728).

It is to be appreciated that FIG. 27 describes software that acts as an intermediary between users and the basic computer resources described in the suitable operating environment 2700. Such software includes an operating system 2718. Operating system 2718, which can be stored on disk storage 2714, acts to control and allocate resources of the computer 2702. Applications 2720 take advantage of the management of resources by operating system 2718 through program modules 2724, and program data 2726, such as the boot/shutdown transaction table and the like, stored either in system memory 2706 or on disk storage 2714. It is to be appreciated that the claimed subject matter can be implemented with various operating systems or combinations of operating systems.

A user enters commands or information into the computer 2702 through input device(s) 2728. Input devices 2728 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2704 through the system bus 2708 via interface port(s) 2730. Interface port(s) 2730 include, for example, a serial port, a parallel port, a game port, and a universal serial bus (USB). Output device(s) 2736 use some of the same type of ports as input device(s) 2728. Thus, for example, a USB port can be used to provide input to computer 2702 and to output information from computer 2702 to an output device 2736. Output adapter 2734 is provided to illustrate that there are some output devices 2736 like monitors, speakers, and printers, among other output devices 2736, which require special adapters. The output adapters 2734 include, by way of illustration and not limitation, video and sound cards that provide a means of connection between the output device 2736 and the system bus 2708. It should be noted that other devices or systems of devices provide both input and output capabilities such as remote computer(s) 2738.

Computer 2702 can operate in a networked environment using logical connections to one or more remote computers, such as remote computer(s) 2738. The remote computer(s)

2738 can be a personal computer, a server, a router, a network PC, a workstation, a microprocessor based appliance, a peer device, a smart phone, a tablet, or other network node, and typically includes many of the elements described relative to computer 2702. For purposes of brevity, only a memory storage device 2740 is illustrated with remote computer(s) 2738. Remote computer(s) 2738 is logically connected to computer 2702 through a network interface 2742 and then connected via communication connection(s) 2744. Network interface 2742 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2744 refers to the hardware/software employed to connect the network interface 2742 to the bus 2708. While communication connection 2744 is shown for illustrative clarity inside computer 2702, it can also be external to computer 2702. The hardware/software necessary for connection to the network interface 2742 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components; and
   a processor that executes the computer executable components stored in the memory, wherein the computer executable components comprise:
   a reception component that receives one or more scout images captured of an anatomical region of a patient in association with performance of a computed tomography scan of the anatomical region of the patient, wherein the anatomical region comprises one or more organs;
   a dose estimation component that employs one or more first machine learning models to estimate, based on the one or more scout images, expected organ doses representative of expected radiation doses exposed to the one or more organs under different automatic exposure control patterns for the computed tomography scan; and
   a quality estimation component that employs one or more second machine learning models to estimate, based on the one or more scout images, expected measures of image quality in a target region and a background region of computed tomography scans captured under the different automatic exposure control patterns.

2. The system of claim 1, wherein the computer executable components further comprise:
   an optimization component that determines an optimal automatic exposure control pattern of the different automatic exposure control patterns for the performance of the computed tomography scan based on the expected organ doses and the expected measures of image quality in a target region, wherein the optimal automatic exposure control pattern maximizes image quality in the target region and minimizes radiation doses to the one or more organs.

3. The system of claim 1, wherein the one or more first machine learning models comprise a deep learning model trained using a supervised machine learning process and ground truth data comprising a plurality of computed tomography volumes generated from computed tomography scans of the anatomical region under the different automatic exposure control patterns and organ segmentation dose maps generated from the plurality of computed tomography volumes.

4. The system of claim 3, wherein the computer executable components further comprise:
   a training component that trains the deep learning model using the supervised machine learning process.

5. The system of claim 1, wherein the one or more second machine learning models comprise a deep learning model trained using a supervised machine learning process and ground truth image quality data generated using a plurality of computed tomography volumes generated from computed tomography scans of the anatomical region under the different automatic exposure control patterns, wherein the ground truth image quality data provides measures of image quality in the target region and the background region as represented in the plurality of computed tomography volumes under the different automatic exposure control patterns.

6. The system of claim 5, wherein the computer executable components further comprise:
   a training component that trains the deep learning model using the supervised machine learning process.

7. The system of claim 5, wherein the computer executable components further comprise:
   a simulation component that generates simulated noise projections using the computed tomography scans and generates the ground truth image quality data based on the simulated noise projections.

8. The system of claim 1, wherein the quality estimation component determines the target region and the background region based on a defined clinical task associated with the performance of the computed tomography scan, and wherein the target region and the background region vary for different clinical tasks.

9. The system of claim 8, wherein a deep learning model is trained to determine optimal automatic exposure control patterns for combinations of the one or more scout images and different clinical tasks.

10. The system of claim 1, wherein the different automatic exposure control patterns reflect different tube current modulations.

11. The system of claim 1, wherein the different automatic exposure control patterns reflect different acquisition parameter values for one or more acquisition parameters selected from a group consisting of: tube voltage, collimation, filtration, bowtie, pitch, and start angle.

12. A method comprising:
receiving, by a system operatively coupled to a processor, one or more scout images captured of an anatomical region of a patient in association with performance of a computed tomography scan of the anatomical region of the patient, wherein the anatomical region comprises one or more organs;
employing, by the system, one or more first machine learning models to estimate, based on the one or more scout images, expected organ doses representative of expected radiation doses exposed to the one or more organs under different automatic exposure control patterns for the computed tomography scan; and
employing, by the system, one or more second machine learning models to estimate, based on the one or more scout images, expected measures of image quality in a target region and a background region of computed tomography scans captured under the different automatic exposure control patterns.

13. The method of claim 12, further comprising:
determining, by the system, an optimal automatic exposure control pattern of the different automatic exposure control patterns for the performance of the computed tomography scan based on the expected organ doses and the expected measures of image quality in a target region, wherein the optimal automatic exposure control pattern maximizes image quality in the target region and minimizes radiation doses to the one or more organs.

14. The method of claim 12, further comprising:
training, by the system, the one or more first machine learning models using a supervised machine learning process and ground truth data comprising a plurality of computed tomography volumes generated from computed tomography scans of the anatomical region under the different automatic exposure control patterns and organ segmentation dose maps generated from the plurality of computed tomography volumes.

15. The method of claim 12, further comprising:
training, by the system, the one or more second machine learning models using a supervised machine learning process and ground truth image quality data generated using a plurality of computed tomography volumes generated from computed tomography scans of the anatomical region under the different automatic exposure control patterns, wherein the ground truth image quality data provides measures of image quality in the target region and the background region as represented in the plurality of computed tomography volumes under the different automatic exposure control patterns.

16. The method of claim 15, further comprising:
generating, by the system, simulated noise projections using the computed tomography scans; and
generating, by the system, the ground truth image quality data based on the simulated noise projections.

17. The method of claim 12, further comprising:
determining, by the system, the target region and the background region based on a defined clinical task associated with the performance of the computed tomography scan, and wherein the target region and the background region vary for different clinical tasks.

18. The method of claim 17, further comprising:
training, by the system, a deep learning model to determine optimal automatic exposure control patterns for combinations of the one or more scout images and different clinical tasks.

19. A machine-readable storage medium, comprising executable instructions that, when executed by a processor, facilitate performance of operations, comprising:
receiving one or more scout images captured of an anatomical region of a patient in association with performance of a computed tomography scan of the anatomical region of the patient, wherein the anatomical region comprises one or more organs;
employing one or more first machine learning models to estimate, based on the one or more scout images, expected organ doses representative of expected radiation doses exposed to the one or more organs under different automatic exposure control patterns for the computed tomography scan; and
employing one or more second machine learning models to estimate, based on the one or more scout images, expected measures of image quality in a target region and a background region of computed tomography scans captured under the different automatic exposure control patterns.

20. The machine-readable storage medium of claim 19, wherein the operations further comprise:
determining an optimal automatic exposure control pattern of the different automatic exposure control patterns for the performance of the computed tomography scan based on the expected organ doses and the expected measures of image quality in a target region, wherein the optimal automatic exposure control pattern maximizes image quality in the target region and minimizes radiation doses to the one or more organs.

* * * * *